United States Patent
Copland et al.

(10) Patent No.: US 8,361,721 B2
(45) Date of Patent: Jan. 29, 2013

(54) METHODS FOR DETECTING, DIAGNOSING AND TREATING HUMAN RENAL CELL CARCINOMA

(75) Inventors: John A. Copland, Ponte Vedra Beach, FL (US); Bruce A. Luxon, Galveston, TX (US); Christopher G. Wood, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/136,588

(22) Filed: Aug. 4, 2011

(65) Prior Publication Data
US 2011/0294694 A1    Dec. 1, 2011

Related U.S. Application Data

(63) Continuation of application No. 10/938,973, filed on Sep. 10, 2004, now abandoned.

(60) Provisional application No. 60/539,838, filed on Jan. 28, 2004, provisional application No. 60/502,038, filed on Sep. 10, 2003.

(51) Int. Cl.
*C12Q 1/68* (2006.01)
(52) U.S. Cl. ........................... 435/6.1; 435/6.14
(58) Field of Classification Search ................... None
See application file for complete search history.

(56) References Cited

U.S. PATENT DOCUMENTS
2003/0224040 A1* 12/2003 Baylin et al. .................. 424/450

OTHER PUBLICATIONS

Gumz et al. (Clin. Cancer Res. Aug. 15, 2007, 13(16): 4740-4749).*
P-SCAN (Peak quantification using Statistical Comparative Analysis, http://abs.cit.nih.gov/pscan/, Jan. 23, 2003).*

* cited by examiner

*Primary Examiner* — Peter J Reddig
(74) *Attorney, Agent, or Firm* — Edwin S. Flores; Chalker Flores, LLP

(57) ABSTRACT

Gene expression profiling and hierarchical clustering analysis readily identify differential gene expressions in normal renal epithelial cells and renal cell carcinomas. Genes identified by this analysis would be useful for diagnosis, prognosis and development of targeted therapy for the prevention and treatment of conventional renal cell carcinoma.

3 Claims, 20 Drawing Sheets

METHODS FOR DETECTING, DIAGNOSING AND TREATING HUMAN RENAL CELL CARCINOMA

CROSS-REFERENCE TO RELATED APPLICATION

This is a continuation application under 35 U.S.C. §120 of nonprovisional application U.S. Ser. No. 10/938,973, filed Sep. 10, 2004, now abandoned, which claims benefit of provisional application U.S. Ser. No. 60/539,838, filed Jan. 28, 2004, now abandoned, and of provisional application U.S. Ser. No. 60/502,038, filed Sep. 10, 2003, now abandoned, the entirety of all of which are hereby incorporated by reference.

BACKGROUND OF THE INVENTION

1. Field of the Invention

The present invention relates generally to the field of cancer research. More specifically, the present invention relates to gene expression profiling for human renal cell carcinoma.

2. Description of the Related Art

Renal cell carcinoma (RCC) represents a major health issue. The American Cancer Society predicts 31,900 new cases will be diagnosed in the United States alone in the year 2003, with 11,900 people dying of the disease. When clinically localized or even locally advanced, renal cell carcinoma can be surgically resected for cure using a variety of approaches. With metastatic progression, however, renal cell carcinoma is incurable, and existing systemic therapies are largely ineffective in impacting disease response or patient survival. The lack of effective systemic therapy for metastatic renal cell carcinoma is, in part, due to a fundamental lack of understanding of the molecular events that result in cellular transformation, carcinogenesis, and progression in human kidney.

The advent of gene array technology has allowed classification of disease states at molecular level by examining changes in all mRNAs expressed in cells or tissues. Gene expression fingerprints representing large numbers of genes may allow precise and accurate grouping of renal cell carcinoma. Moreover, large scale gene expression analysis have the potential of identifying a number of differentially expressed genes in renal cell carcinoma compare to normal renal epithelial cells. These genes or markers may further be tested for clinical utility in the diagnosis and treatment of renal cell carcinoma.

Thus, the identification of novel renal cell carcinoma markers to be used for detection, diagnosis and development of effective therapy against the disease remains a high priority. The prior art is deficient in understanding the molecular differences between renal cell carcinoma and normal renal epithelium. The present invention fulfills this need in the art by providing gene expression profiling for these two types of tissues.

SUMMARY OF THE INVENTION

The present invention identifies genes with a differential pattern of expression between different subtypes of renal cell carcinomas (RCC) and normal renal epithelium. These genes and their products can be used to develop novel diagnostic and therapeutic markers for the treatment of renal cell carcinomas.

Genomic profiling of conventional renal cell carcinoma tissues and patient-matched normal kidney tissue samples was carried out using stringent statistical analyses (ANOVA with full Bonferroni corrections). Subtypes of renal cell carcinoma include stage I, II, III, and IV (reflecting differences in tumor size, lymph node and organ metastasis), stage I papillary renal cell carcinoma, and benign oncocytoma. Hierarchical clustering of the expression data readily distinguished normal tissue from renal cell carcinomas. The identified genes were verified by real-time FCR and immunohistochemical analyses.

Different subtypes of conventional renal cell carcinomas can be diagnosed either by drawing blood and identifying secreted gene products specific to renal cell carcinoma or by doing a biopsy of the tissue and then identify specific genes that are altered when renal cell carcinoma is present. An example of when this may be especially important is in distinguishing the deadly conventional renal cell carcinomas (account for 85% of all renal cell carcinomas) from renal oncocytoma (benign renal cell carcinoma) as well as identifying the histologic subtypes of papillary and sarcomatoid renal cell carcinoma. Identification of specific genes will also help in determining which patients will have a good prognosis verses that of a poor prognosis. In addition, subsets of genes identified in the present invention can be developed as targets for therapies that could cure, prevent, or stabilize the disease. Thus, results from the present invention could be used for diagnosis, prognosis, and development of therapies to treat or prevent renal cell carcinoma.

In one embodiment, there are provided methods of detecting conventional or clear cell renal cell carcinoma based on over-expression and/or down-regulation of a number of genes disclosed herein. In another embodiment, conventional or clear cell renal cell carcinoma is detected based on decreased expression of type III TGF-β receptor.

In yet another embodiment, there are provided methods of detecting stage I conventional or clear cell renal cell carcinoma based on over-expression and/or down-regulation of a number of genes disclosed herein.

The present invention also provides methods of detecting stage II conventional or clear cell renal cell carcinoma based on over-expression and/or down-regulation of a number of genes disclosed herein.

The present invention also provides methods of detecting papillary renal cell carcinoma or benign oncocytoma based on over-expression and/or down-regulation of a number of genes disclosed herein.

In another embodiment, there is provided a method of targeting conventional or clear cell renal cell carcinoma cells based on generating antibodies or small molecules directed against a cell surface molecule over-expressed in conventional renal cell carcinoma cells.

In yet another embodiment, there is provided a method of treating conventional or clear cell renal cell carcinoma by replacing down-regulated tumor suppressor gene in conventional renal cell carcinoma.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 11A shows gene array data from 10 patients—five diagnosed with localized renal cell carcinoma and five with metastatic disease. '+' (P<0.05) indicates statistical difference for TBR3 mRNA levels as compared to normal tissue and '*' (P<0.28) indicates statistical difference for TBR2 mRNA levels as compared to normal controls. Data are expressed as mean±s.e. FIG. 11B shows real-time RT-PCR verification of TBR1, TBR2, and TBR3 mRNA levels of tissue samples described in FIG. 11A. Data are expressed as mean±s.d.

FIG. 14A shows semi-quantitative RT-PCR measurements of mRNA levels of TBR1, TBR2, and TBR3 for UMRC3, UMRC6 and normal renal epithelial (NRE) cells. FIG. 14B shows immunohistochemistry of protein expression for TBR1, TBR2, and TBR3 (×40 magnification).

FIG. 15A shows cell proliferation was inhibited as assessed by DNA content 3 days after αtreatment. Percent of each respective untreated control was used for comparisons. Transient transfection using 3TP/Ix along with a renilla luciferase control demonstrates loss of responsiveness to 2 ng/ml TGF-β1 with loss of TGF-β receptor expression (FIG. 15B). Firefly luciferase activity was normalized using the ratio of firefly luciferase/renilla luciferase. Data are expressed as mean±s.d.

DETAILED DESCRIPTION OF THE INVENTION

Figure 1A:
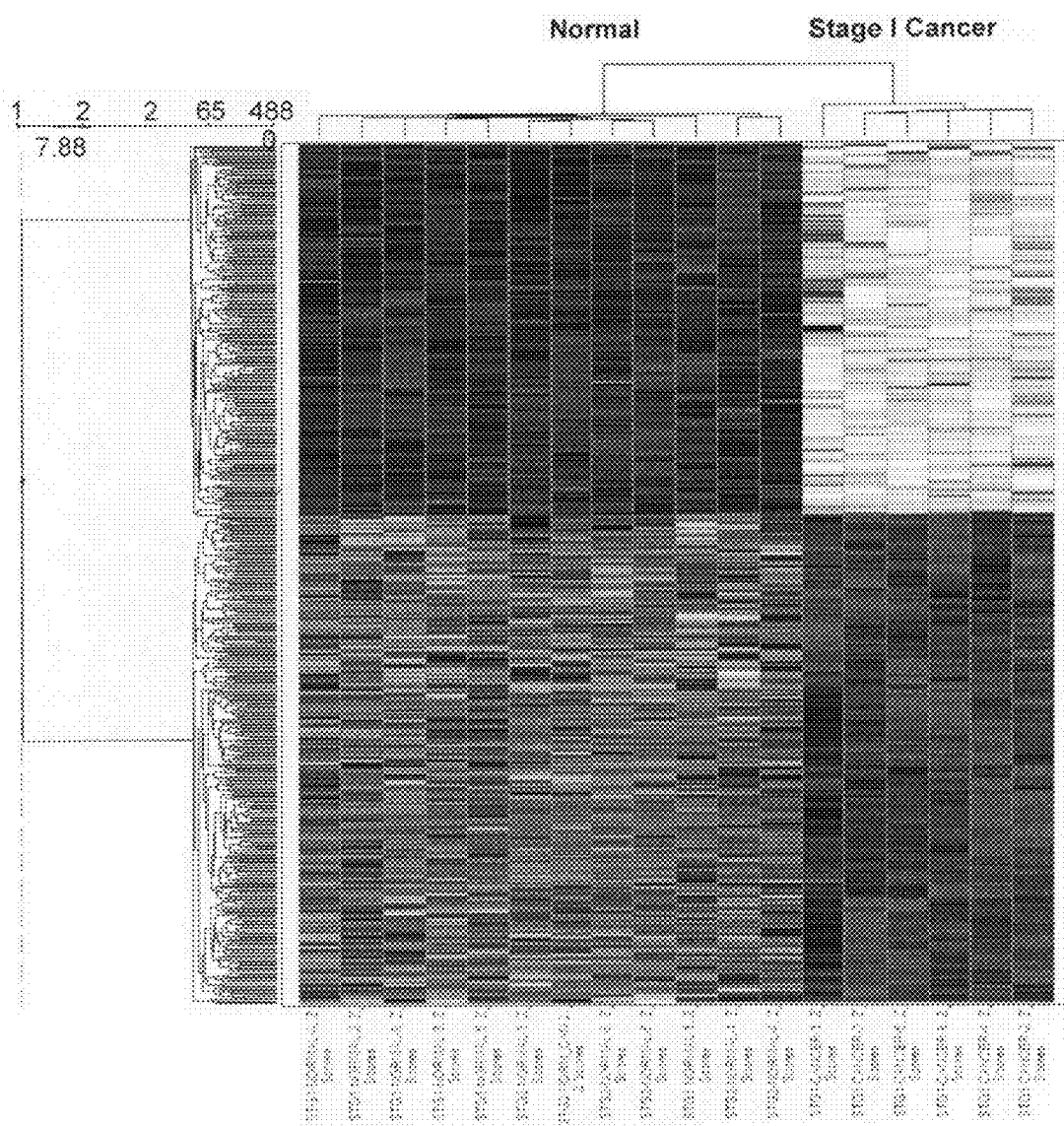
FIG. 1A shows hierarchical clustering of genes expressed in normal renal cortex (12 patient tissue samples) verse stage I conventional renal cell carcinoma (6 patient tissue samples). Red indicates that a gene is highly expressed and green is indicative of low expression. Four hundred eighty eight genes were depicted in FIG. 1A.

High-throughput technologies for assaying gene expression, such as high-density oligonucleotide and cDNA microarrays, offer the potential to identify clinically relevant genes differentially expressed between normal and tumor cells. The present invention discloses a genome-wide examination of differential gene expression between renal cell carcinomas (RCC) and normal renal epithelial cells.

Currently, there are no proven molecular markers useful clinically for the diagnosis, staging, or prognosis of sporadic renal cell carcinoma. The present invention detects genes that have differential expression between renal cell carcinomas and normal renal epithelial cells. The known function of some of these genes may provide insight into the biology of renal cell carcinomas while others may prove to be useful as diagnostic or therapeutic markers against renal cell carcinomas. Subtypes of renal cell carcinomas disclosed herein include stage I, II, III, and IV renal cell carcinomas (reflecting differences in tumor size, lymph node and organ metastasis), stage I papillary renal cell carcinoma, and benign oncocytoma.

The present invention provides methods of detecting conventional renal cell carcinoma based on determining the expression level of a number of genes that are found to have 2-fold or higher differential expression levels between tumor and normal tissue. In general, biological samples (e.g. tissue samples, serum samples, urine samples, saliva samples, blood samples or biopsy samples) are obtained from the individual to be tested and gene expression at RNA or protein level is compared to that in normal tissue. The normal tissue samples can be obtained from the same individual who is to be tested for renal cell carcinoma. It will be obvious to one of ordinary skill in the art that gene expression can be determined by DNA microarray and hierarchical cluster analysis, real-time PCR, RT-PCR, or northern analysis, whereas secreted gene products can be measured in blood samples by standard procedures.

In one embodiment, there is provided a method of detecting conventional or clear cell renal cell carcinoma based on differential expression of one or more of the following genes or proteins: TGF-β1, TGF-α, adrenomedulin, fibroblast growth factor 2 (FGF2), vascular epidermal growth factor (VEGF), osteonectin, follistatin like-3, inhibin beta A, spondin 2, chemokine X cytokine receptor 4 (CXCR4), fibronectin, neuropilin 1, frizzled homolog 1, insulin-like growth factor binding protein 3, laminin alpha 3, integrin beta 2, semaphorins 6A, semaphorins 5B, semaphorins 3B, caspase 1, sprouty 1, CDH16, PCDH9, compliment component 1-beta, compliment component 1-alpha, compliment component 1-gamma, CD53, CDW52, CD163, CD14, CD3Z, CD24, RAP1, angiopoietin 2, cytokine knot secreted protein, MAPKKKK4, 4-hydroxyphenylpyruvate dioxygenase, pyruvate carboxyknase 2, 11-beta-hydroxysteroid dehydrogenase 2, GAS1, CDKN1, nucleolar protein 3, interferon induced protein 44, NR3C1, vitamin D receptor, hypothetical protein FLJ14957 (Affy#225817_at), metallothionein 2A, metallothionein-If gene, metallothionein 1H, secreted frizzled related protein 1, connective tissue growth factor, and epidermal growth factor.

In another embodiment, there is provided a method of detecting conventional renal cell carcinoma by examining the expression level of type III TGF-β receptor, wherein decreased expression of type III TGF-b receptor indicates the presence of renal cell carcinoma. In general, the expression level of type III TGF-β receptor can be determined at the mRNA or protein level.

The present invention also provides methods of detecting stage I conventional renal cell carcinoma, stage II conventional renal cell carcinoma, stage I papillary renal cell carcinoma, or benign oncocytoma based on over-expression or down-regulation of a number of genes identified in the present invention. The present invention discloses a number of genes that are up- or down-regulated specifically in these subtypes of renal cell carcinoma. Determining the expression levels of these genes would provide specific diagnosis for these different subtypes of renal cell carcinoma.

For example, stage I conventional renal cell carcinoma can be detected based on (i) over-expression of one or more genes listed in Table 1, (ii) down-regulation of one or more genes listed in Table 2, or (iii) over-expression of one or more genes listed in Table 1 and down-regulation of one or more genes listed in Table 2. Similarly, stage II conventional renal cell carcinoma can be detected based on (i) over-expression of one or more genes listed in Table 3, (ii) down-regulation of one or more genes listed in Table 4, or (iii) over-expression of one or more genes listed in Table 3 and down-regulation of one or more genes listed in Table 4.

The present invention also discloses a number of genes that are up- or down-regulated in both stage I and stage II conventional renal cell carcinoma (Tables 5 and 6 respectively). These genes would also provide diagnosis for stage I or stage II conventional renal cell carcinoma. Hence, stage I or stage II conventional renal cell carcinoma can be detected based on (i) over-expression of one or more genes listed in Table 5, or (ii) down-regulation of one or more genes listed in Table 6.

In another embodiment, stage I papillary renal cell carcinoma can be detected based on (i) over-expression of one or more genes listed in Table 8, (ii) down-regulation of one or more genes listed in Table 9, or (iii) over-expression of one or more genes listed in Table 8 and down-regulation of one or more genes listed in Table 9.

In yet another embodiment, benign oncocytoma can be detected based on (i) over-expression of one or more genes listed in Table 10, (ii) down-regulation of one or more genes listed in Table 11, or (iii) over-expression of one or more genes listed in Table 10 and down-regulation of one or more genes listed in Table 11.

In still yet another embodiment, there are provided methods of utilizing genes over-expressed on the cell surface of renal carcinoma tissue to develop antibodies or other small molecules for the purpose of specifically targeting the renal tumor cells. The present invention discloses a number of genes that are up-regulated in stage I renal cell carcinoma (RCC), stage II RCC tumor, stage I papillary RCC, and benign oncocytoma. Antibodies or small molecules directed against proteins encoded by these genes can be linked with a therapeutic drug to deliver drug to the tumor tissue, or be linked with dye, nanoparticle or other imaging agents for cancer imaging. Some of the novel genes identified herein for the first time include, but are not limited to, the following genes: calcitonin receptor-like (206331_at; 210815_s_at); receptor (calcitonin) activity modifying protein 2 (RAMP2; 205779_at); endothelin receptor type B (206701_x_at); beta 2 integrin (202803_s_at); alpha 5 integrin (201389_at); chemokine X cytokine receptor 4 (CXCR4); fibronectin; neuropilin 1 (212298_at; 210510_s_at); CD24; CD14; Cd163; CD53; Compliment Componenet 1-beta, 1-alpha, and 1-gamma; CDH4; integrin beta2; ADAM28; FK506 binding protein; collagen Valpha2; tumor necrosis factor receptor superfamily, member 6; tumor necrosis factor receptor superfamily, member 5; tumor necrosis factor (ligand) superfamily, member 13b; tumor necrosis factor receptor superfamily, member 12A; and the FGF receptor.

In another embodiment, there is provided a method of treating conventional or clear cell renal cell carcinoma. The method involves replacing tumor suppressor genes (e.g., via gene therapy) whose expression is down-regulated in tumor tissues or introducing a molecule that induces the down-regulated gene to be re-expressed in the tumor. The present invention discloses a number of genes that are down-regulated in stage I renal cell carcinoma (RCC), stage II RCC tumor, stage I papillary RCC, and benign oncocytoma. Some examples of down-regulated genes identified in stage I and/or II RCC tumors include, but are not limited to, CDKN1, secreted frizzled related protein 1, semaphoring 6D, semaphoring 3B, CDH16, TNF alpha, calbindin D28, defensin beta1, beta-catenin interacting protein 1, GAS1, vitamin D receptor, Kruppel-like factor 15. This method of treatment can be combined with other therapies to provide combinatorial therapy.

The genes that are found to have altered expression in stage I and stage II renal cell carcinoma would also be useful for determining patient prognosis. These genes or gene products (i.e., proteins) would have the unique characteristic of being altered in tumor verses normal samples in a subset of patients. For example, basic transcription element binding protein 1 is down-regulated in 7 out of 12 renal cell carcinoma tumors. Other examples include CD164, decreased 5/12; Map kinase kinase kinase 7, increased 6/12; Endoglin, increased 7/12; SERPIN A1, increased 6/12; Metalloprotease 11 (MMP11), increased 7/12; Integrin 3 alpha, increased 4/12; carbonic anhydrase II, decreased 7/12; protein tyrosine kinase 2, increased 4/12; fibroblast growth factor 11, increased 6/12; fibroblast growth factor 2, increased 7/12; VEGF B, increased 5/12.

Moreover, the levels of change may be a useful determinant of patient outcome and/or rationale for strategy of treatment course. An example of this is found for chemokine (C—X—C motif) ligand 14 (CXCL14, 222484_s_at). Six patients with stage I and six patients with stage II renal cell carcinoma were analyzed by genomic profiling. A patient with stage I renal cell carcinoma has CXCL14 mRNA expression levels of 19862 and 24.49 in his normal tissue and tumor tissue respectively. This patient would be predicted to have a poor prognosis or poor response to therapy based upon this result along with other gene predictors. On the other hand, a patient with stage II RCC has CXCL14 mRNA expression levels of 20435 and 18557 in his normal tissue and tumor tissue respectively. This patient would be predicted to have a good prognosis and good response to chemotherapy.

The following examples are given for illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Tissue Banking

Renal tissue (normal and tumor) was transported to a sterile hood on ice and under sterile conditions. Tissue was dissected under the direction of a pathologist. The tissue was frozen in liquid nitrogen for isolation of RNA, DNA, and protein or processed to establish primary cell cultures. The tissue was fixed in formalin for immunohistochemistry and in situ hybridization and RNAlater (Ambion) for RNA isolation. Primary normal renal epithelial (NRE) cell cultures were established using standard collagenase/Dnase techniques to digest tissue and isolate single cells. NREs were easily isolated and grew well in culture for up to 10 passages. These cells were further analyzed for homogeneity with regard to epithelial population using appropriate immunohistochemical markers such as vimentin, cytokeratin, and megalin.

EXAMPLE 2

Genomic Gene Array and Microarray Data Analysis

Gene expression profiling was performed using Affymetrix HU95A oligonucleotide gene arrays (>12,600 genes) or HG-U133 A&B GeneChip® oligonucleotide microarrays (33,000+ probe sets). Total RNA (Trizol®, Ambion) was extracted from patient-matched normal renal cortex and tumor tissue from patients diagnosed with local disease confined to the kidney. Alternatively, the investigators analyzed metastatic disease defined by lesions in lymph nodes, adrenal, or other organs. Data were analyzed by a combination of two-dimensional ANOVA, Affymetrix MAS5.0®, and hierarchical cluster analysis using Spotfire®. Procedure that were used to identify altered expression of large sets of genes, as well as other issues concerning microarray analyses can be found in a recent review article by Copland et al. (2003).

EXAMPLE 3

Real-Time PCR

Applied Biosystems' assays-by-design or assays-on-demand 20× assay mix of primers and TaqMan® MGB probes (FAM® dye-labeled) for all target genes and predeveloped 18S rRNA (VIC® dye-labeled probe) TaqMan® assay reagent for internal control were used for real-time PCR measurements. These assays were designed to span exon-exon junctions so as not to detect genomic DNA and all primers and probes sequences were searched against the Celera database to confirm specificity. Validation experiments were performed to test the efficiency of the target amplification and the efficiency of the reference amplification. All absolute values of the slope of log input amount versus $DC_T$ is less than 0.1.

Separate tubes (singleplex) for one-step RT-PCR was performed with 50 ng RNA for both target genes and endogenous controls using TaqMan® one-step RT-PCR master mix reagent kit (Applied Biosystems). The cycling parameters for one-step RT-PCR were: reverse transcription 48° C. for 30 min, AmpliTaq® activation 95° C. for 10 min, denaturation 95° C. for 15 s, and annealing/extension 60° C. for 1 min (repeat 40 times) on ABI7000®. Duplicate $C_T$ values were analyzed with Microsoft Excel® using the comparative $C_T(DDC_T)$ method as described by the manufacturer (Applied Biosystems). The amount of target ($2^{-DDCT}$) was obtained by normalizing to an endogenous reference (18sm-RNA) and relative to a calibrator (normal tissue).

EXAMPLE 4

Immunohistochemical Analyses of Protein Expression

For immunohistochemical analyses of type I TGF-β receptor (TBR1), type II TGF-β receptor (TBR2), and type III TGF-β receptor (TBR3) expression, patient-matched normal renal and tumor tissue samples were fixed in 10% neutral-buffered formalin and embedded in paraffin blocks. Consecutive sections were cut 5 um thick, deparaffinized, hydrated, and immunostained using antibodies recognizing human TBR1, TBR2, and TBR3 (1:100; Santa Cruz Biotechnology). Biotinylated secondary antibody (1:600; Santa Cruz Biotechnology) was detected using avidin-biotin-peroxidase detection according to the manufacturer's instructions (Vectastatin Elite ABC kit; Vector Lab). All slides were lightly counterstained with hematoxylin before dehydration and mounting.

For cell lines, cells were plated on glass coverslips in wells. Prior to the detection of TGF-β receptor expression as described above, cells were fixed onto the coverslips with 3% formalin.

EXAMPLE 5

Gene Expression Profiling of Renal Cell Carcinoma

Gene expression profiling was performed using Affymetrix oligonucleotide gene arrays. RNA was extracted from patient-matched normal renal cortical and tumor tissues from patients diagnosed with localized and metastatic renal cell carcinoma. Data were analyzed by a combination of two-dimensional ANOVA, Affymetrix MAS5.0®, and hierarchical cluster analysis using Spotfire® (reviewed in Copland et al., 2003).

A primary goal of microarray analysis is to discover hidden patterns of differential expression within a large data field. Normal renal cortical and primary tumor tissue with no metastasis were collected from patients diagnosed with local disease. Normal tissue, primary tumor, and metastatic tissue were also collected from patients diagnosed with metastatic disease. Comparison of patient-matched normal and tumor tissue allowed for the discovery of changes in mRNA levels between normal and tumor tissue, as well as local and metastatic disease.

Figure 1B:
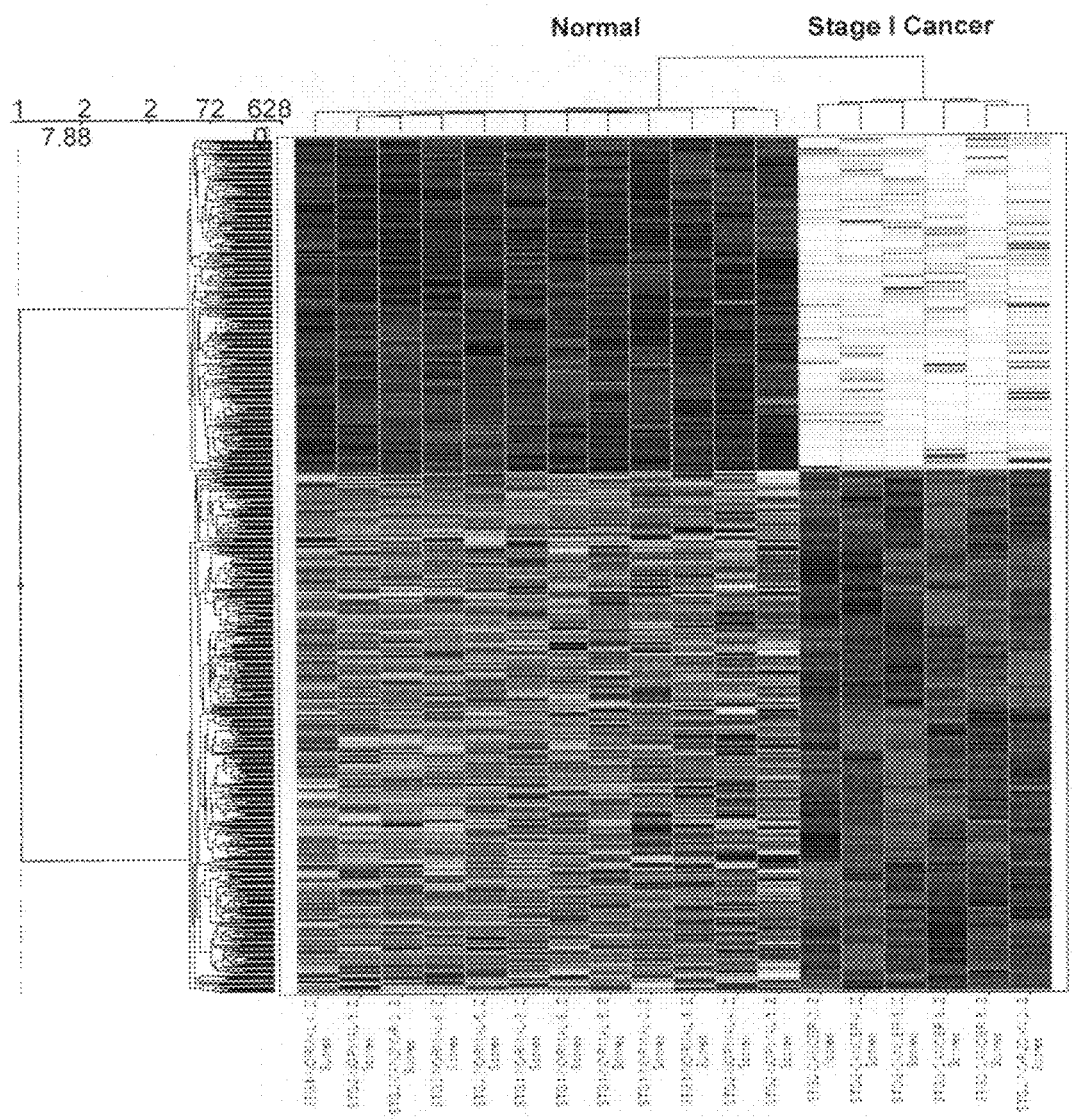
FIG. 1B shows hierarchical clustering of genes expressed in normal renal cortex (12 patient tissue samples) verse stage II conventional renal cell carcinoma (6 patient tissue samples). Red indicates that a gene is highly expressed and green is indicative of low expression. Six hundred twenty eight genes were depicted in FIG. 1B.
Figure 1C:
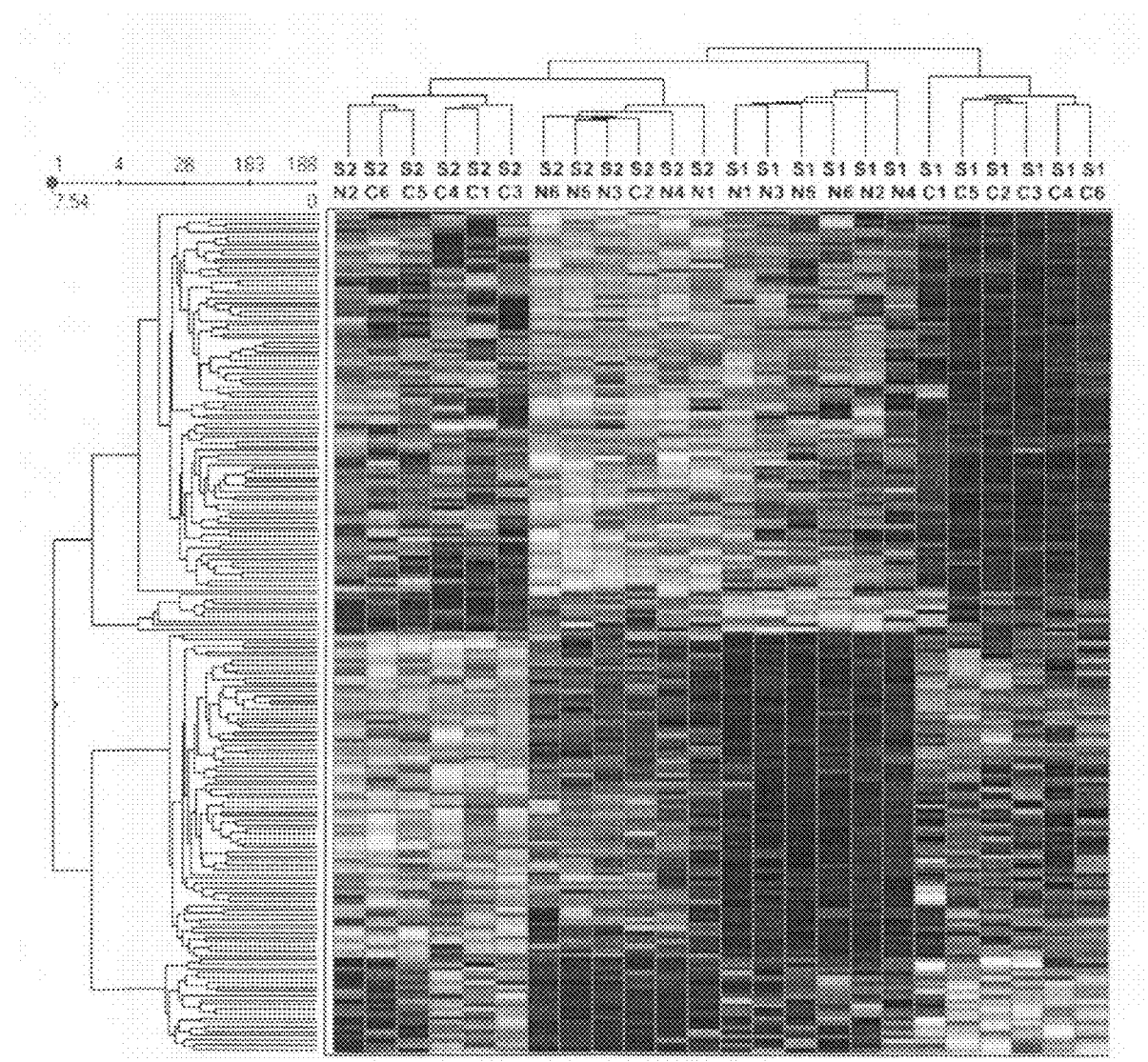
FIG. 1C shows hierarchical clustering of genes selected from a Venn analysis in which the chosen genes were expressed in common in both stage I and II at a 99% confidence level. One hundred eighty eight genes were depicted in FIG. 1C. C, cancer cells; N, normal cells; S1, stage 1; S2, stage 2.

Heatmaps with two-way dendograms depicting genes specifically altered in tumor tissue as compared to normal renal cortex are shown in FIG. 1. FIG. 1A shows hierarchical clustering of genes expressed in normal renal cortex verses stage I conventional renal cell carcinoma. FIG. 1B shows hierarchical clustering of genes expressed in normal renal cortex verses stage II renal cell carcinoma. FIG. 1C shows hierarchical clustering of genes selected from a Venn analysis in which the chosen genes were expressed in common in both stage I and II at a 99% confidence level.

Figure 2:
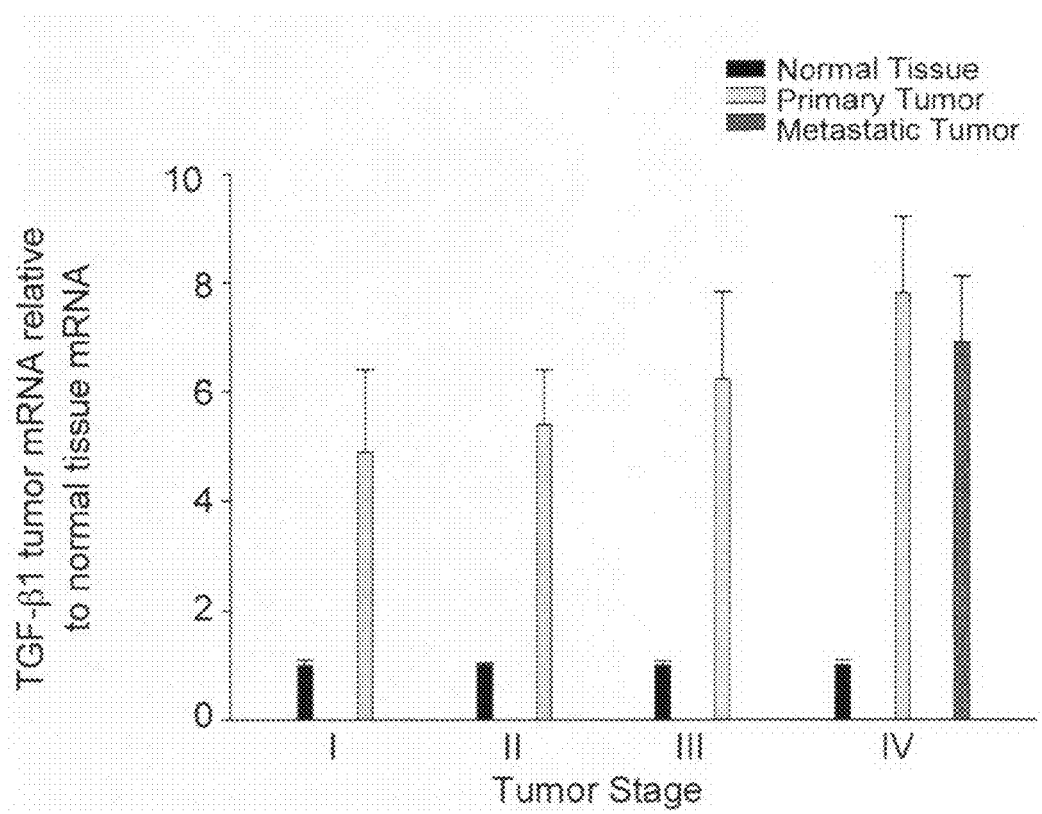
FIG. 2 shows TGF-β1 mRNA expression in stages I-IV renal cell carcinoma as measured by real time PCR TGF-β1 mRNA levels were up-regulated in all stages of renal cell carcinoma as compared to normal tissue counterparts.
Figure 3:
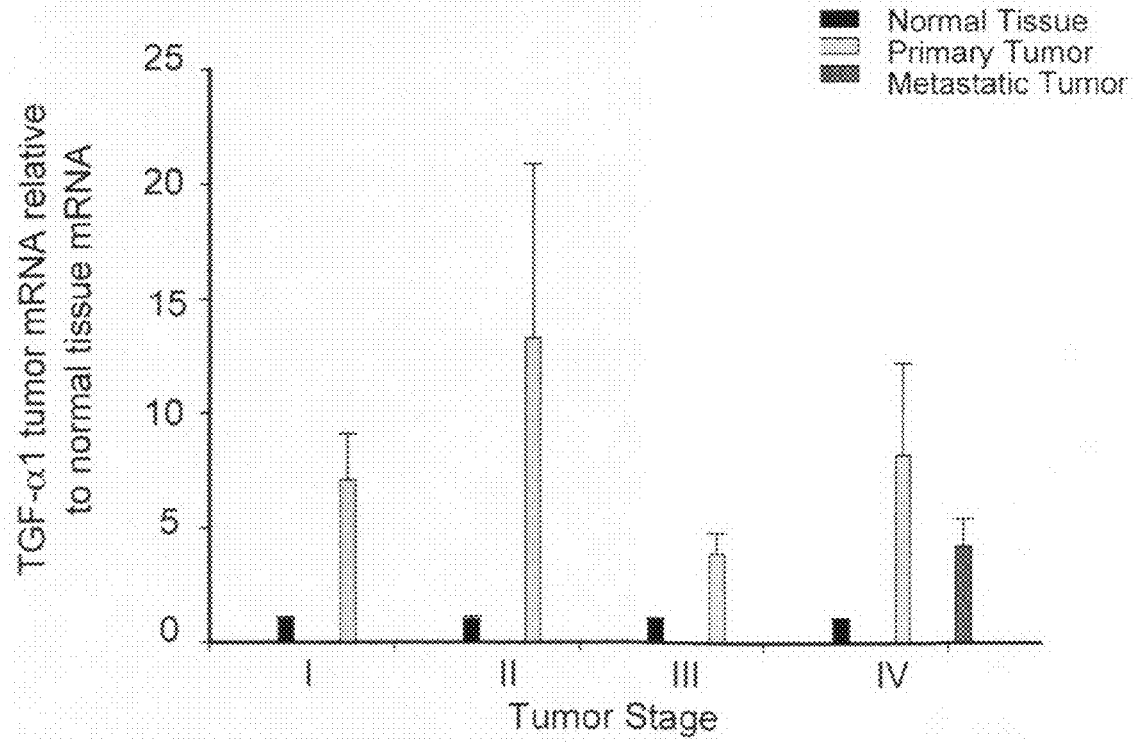
FIG. 3 shows TGF-α mRNA expression in stages I-IV renal cell carcinoma as measured by real time PCR. TGF-α mRNA levels were up-regulated in all stages of renal cell carcinoma as compared to normal tissue counterparts.
Figure 4:
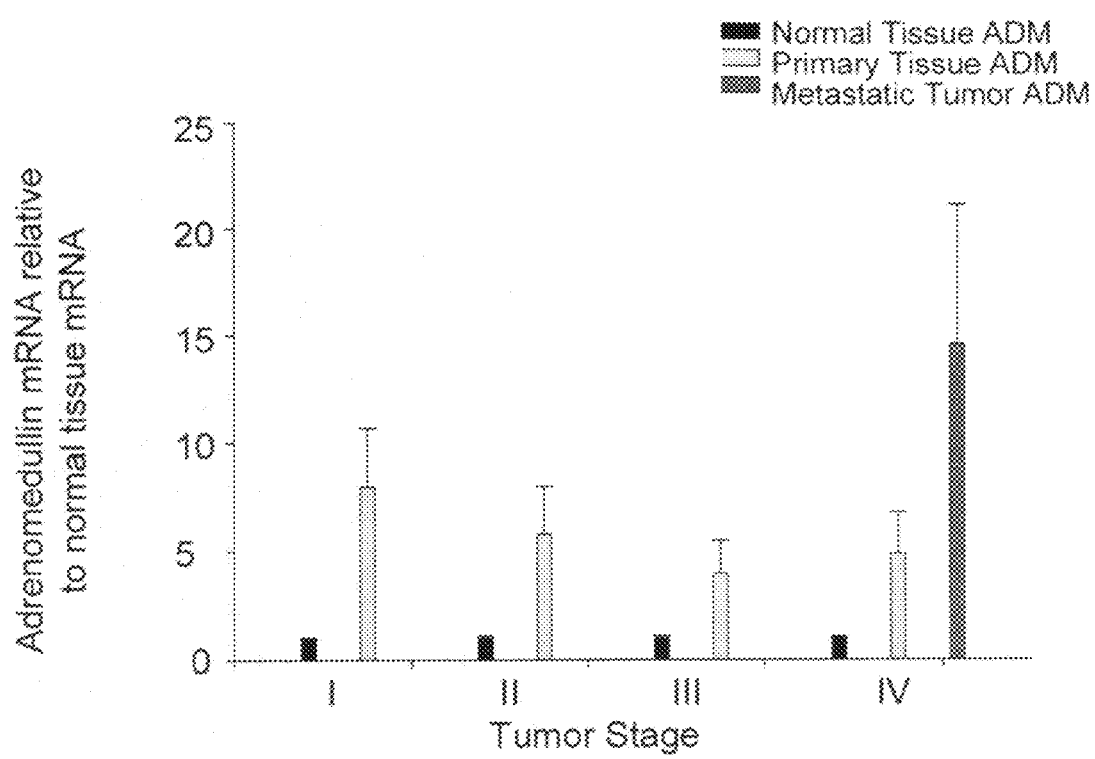
FIG. 4 shows adrenomedulin mRNA expression in stages I-IV renal cell carcinoma as measured by real time PCR. Adrenomedulin mRNA levels were up-regulated in all stages of renal cell carcinoma as compared to normal tissue counterparts.
Figure 5:
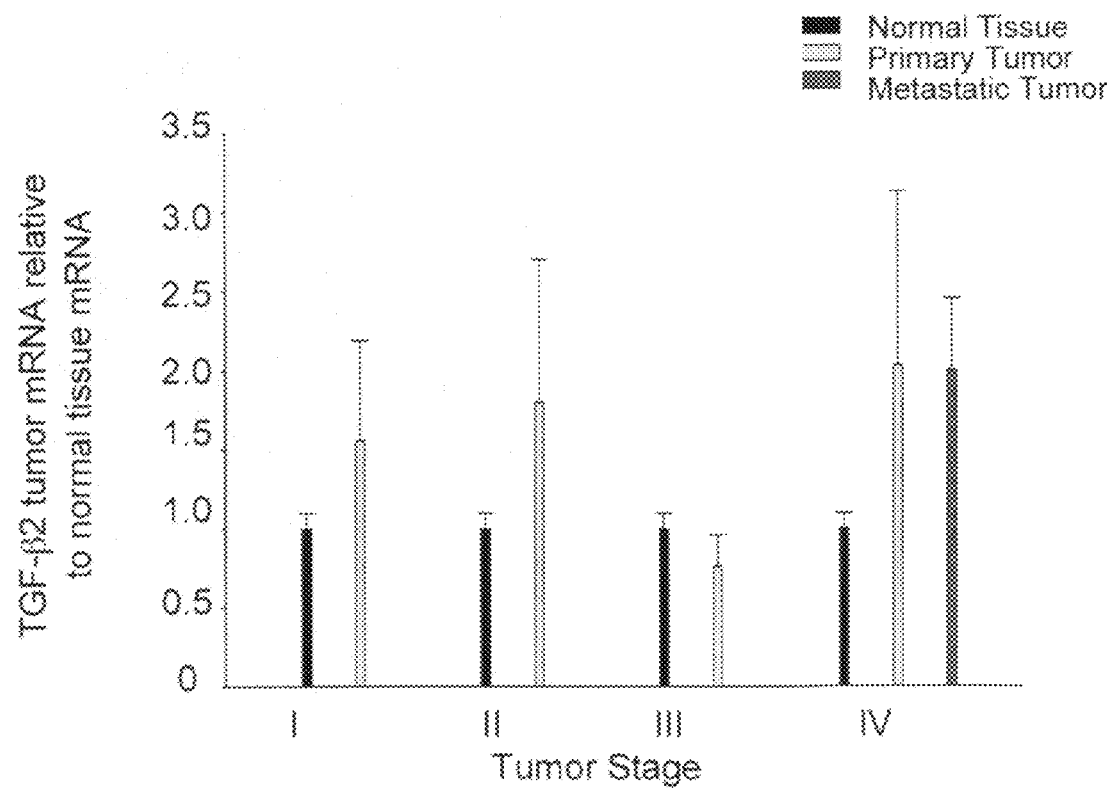
FIG. 5 shows TGF-β2 mRNA expression in stages I-IV renal cell carcinoma as measured by real time PCR. TGF-β2 mRNA levels were not altered between normal and tumor matched samples.
Figure 6:
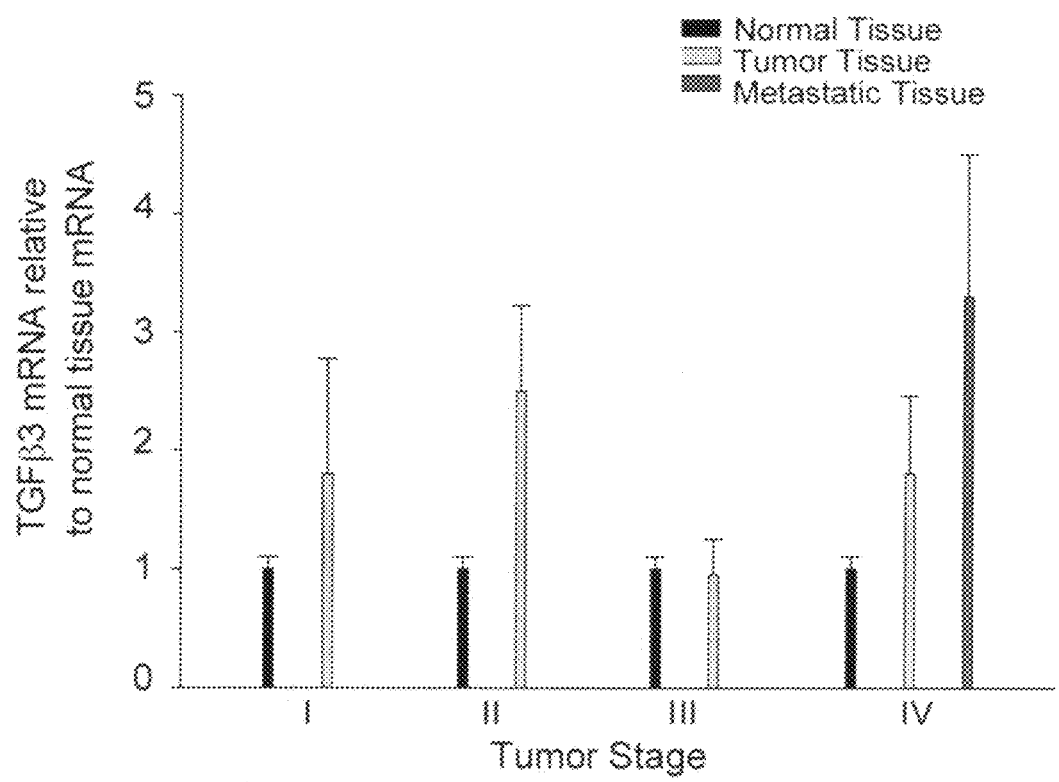
FIG. 6 shows TGF-β3 mRNA expression in stages I-IV renal cell carcinoma as measured by real time PCR. TGF-β3 mRNA levels were not altered between normal and tumor matched samples.

TGF-β1, TGF-α and adrenomedulin mRNA levels were up-regulated in all stages of renal cell carcinoma as compared to normal tissue counterparts (FIGS. 2-4), whereas TGF-β2 and TGF-β3 mRNA levels were not altered between normal and tumor matched samples (FIGS. 5-6).

Figure 7:
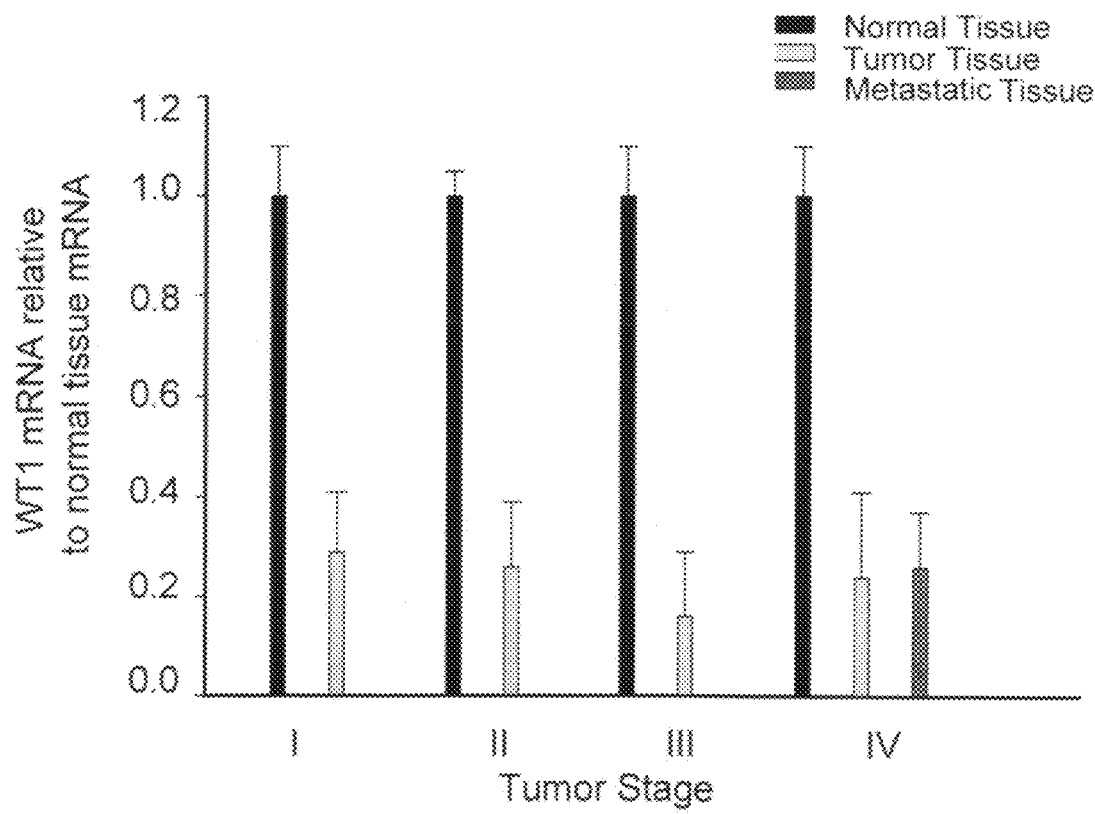
FIG. 7 shows tumor suppressor gene Wilms Tumor 1 (WT1) mRNA expression in stages I-IV renal cell carcinoma as measured by real time PCR. WT1 mRNA levels were down-regulated in all stages of renal cell carcinoma as compared to normal tissue counterparts.
Figure 8:
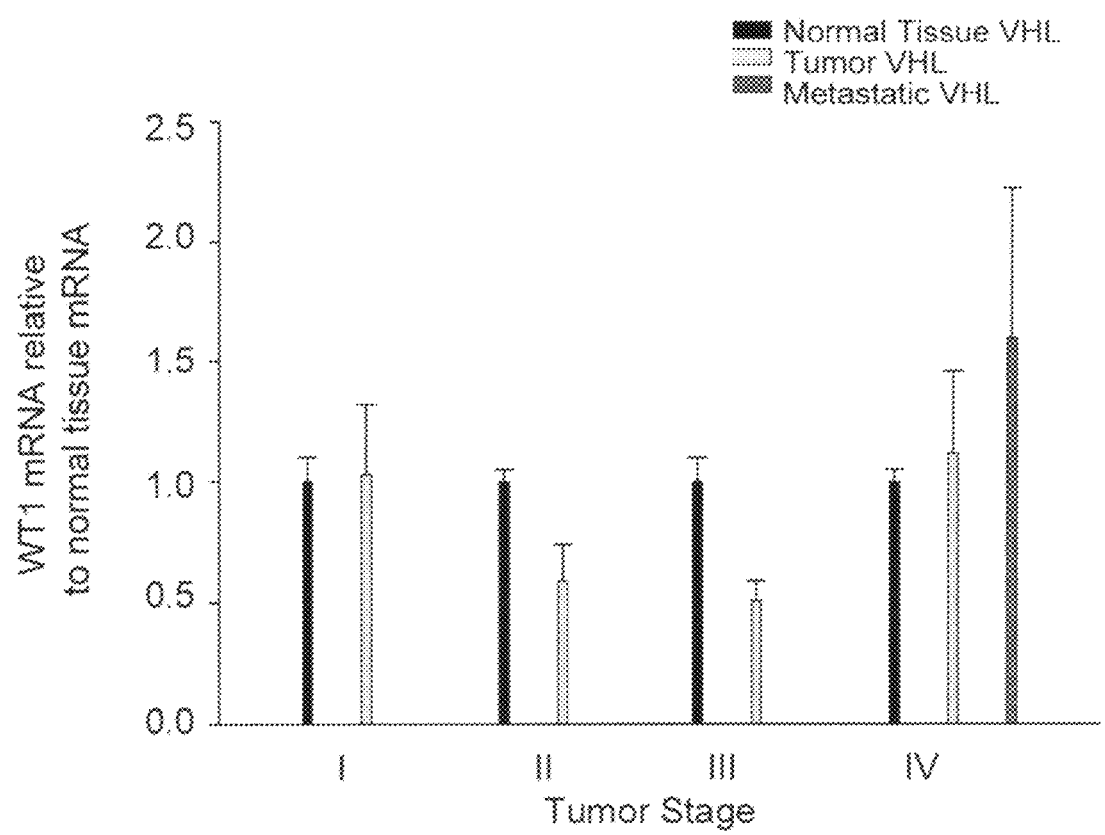
FIG. 8 shows von Hippel Lindau mRNA expression in stages I-IV renal cell carcinoma as measured by real time PCR. A small percentage of tumor tissues demonstrated attenuated von Hippel Lindau mRNA levels when compared to matched normal tissue
Figure 9:
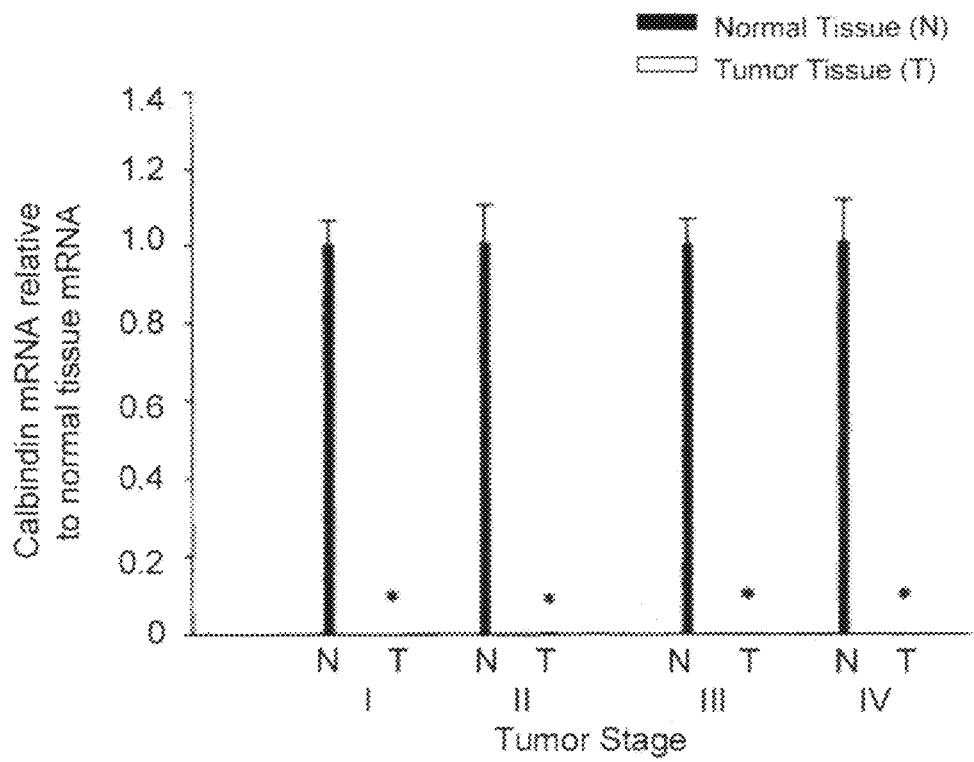
FIG. 9 shows calbindin mRNA expression in stages I-IV renal cell carcinoma as measured by real time PCR. Calbindin mRNA was completely lost in all stage I renal cell carcinoma. p<0.05 compared to matched control. *Stage I tumor: 0±0; stage III tumor: 0.0009±0.0004; stage IV tumor: 0.003±0.0004/
Figure 10:
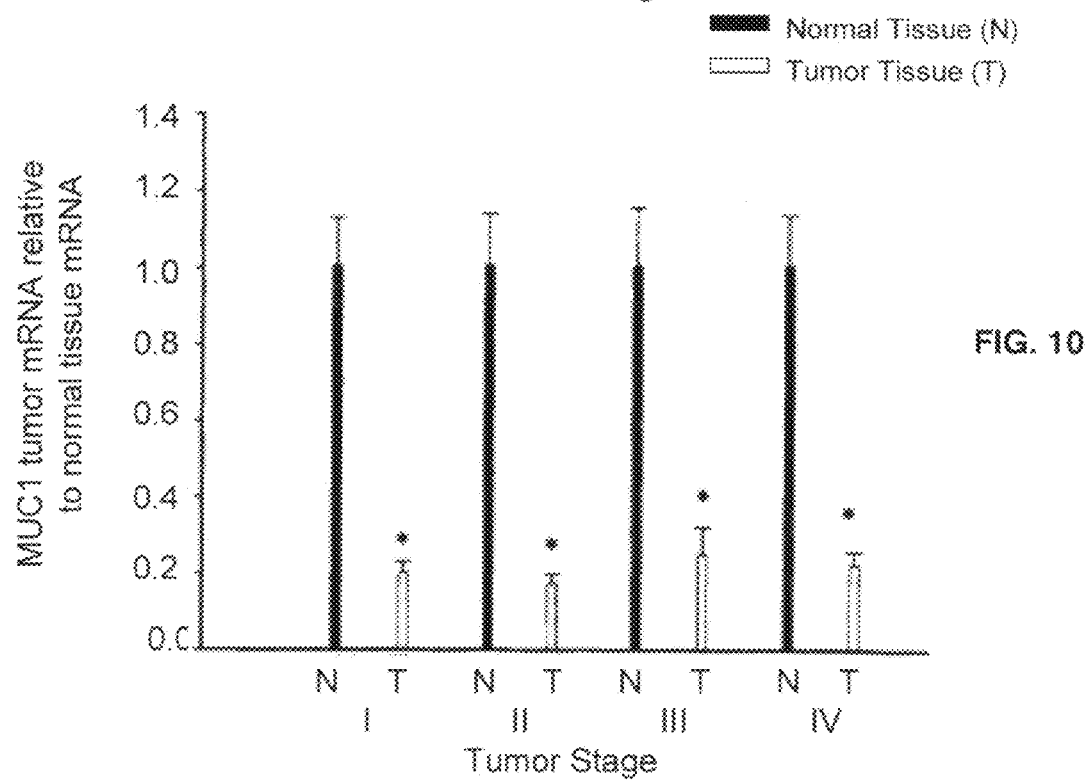
FIG. 10 shows MUC1 mRNA expression in stages I-IV renal cell carcinoma as measured by real time PCR. MUC1 mRNA levels were down-regulated in all tumor tissues as early as stage I. *p<0.05 compared to matched control.

Tumor suppressor gene Wilms Tumor 1 (WT1) was down-regulated in all stages of renal cell carcinoma (FIG. 7). A small percentage of tumor tissues demonstrated attenuated von Hippel Lindau mRNA levels when compared to matched normal tissue (FIG. 8). Calbindin mRNA was completely lost (FIG. 9) while MUC1 was greatly attenuated in stage I renal cell carcinoma (FIG. 10).

The present analysis identifies 278 genes that were up-regulated in stage I renal cell carcinoma, whereas 380 genes were up-regulated in stage II renal cell carcinoma. Among these genes, 82 were up-regulated in both stages I and II renal cell carcinoma. One hundred fifty nine genes were down-regulated in stage I renal cell carcinoma, whereas 195 genes were down-regulated in stage II RCC. Among these genes, 82 were down-regulated in both stage I and II renal cell carcinoma.

Genes over-expressed and down-regulated in stage I renal cell carcinoma are listed in Table 1 and Table 2 respectively. Genes over-expressed and down-regulated in stage I renal cell carcinoma are listed in Table 3 and Table 4 respectively. Genes over-expressed in both stage I and II renal cell carcinoma are listed in Table 5. Genes down-regulated in both stage I and II renal cell carcinoma are listed in Table 6.

TABLE 1

Genes With Up-Regulated Expression In stage I Renal Cell Carcinoma

| Genbank ID | Gene Symbol | Genbank ID | Gene Symbol |
| --- | --- | --- | --- |
| NM004356.1 | CD81 | NM004079.1 | CTSS |
| NM002293.2 | LAMC1 | NM001784.1 | CD97 |
| NM000980.1 | RPL18A | AF151853.1 | PREI3 |
| AK002091.1 | MGEA5 | NM000491.2 | C1QB |
| NM005721.2 | ACTR3 | BC000125.1 | TGFB1 |
| NM002668.1 | PLP2 | NM004520.1 | KIF2 |
| NM021038.1 | MBNL | NM000321.1 | RB1 |
| AF070656.1 | YME1L1 | NM012262.2 | HS2ST1 |
| NM021029.1 | RPL36A | NM000560.1 | CD53 |
| NM002945.1 | RPA1 | NM005502.1 | ABCA1 |
| NM002480.1 | PPP1R12A | AF285167.1 | ABCA1 |
| NM001349.1 | DARS | BG170541 | MET |
| NM005496.1 | SMC4L1 | NM021642.1 | FCGR2A |
| AW163148 | MARCKS | BE967532 | KIAA0220 |
| NM002356.4 | MARCKS | NM006526.1 | ZNF217 |
| M68956.1 | MARCKS | NM000570.1 | FCGR3B |
| AI589086 | LAPTM5 | N26005 | PPP1R3C |
| NM006762.1 | LAPTM5 | NM006153.1 | NCK1 |
| NM014267.1 | SMAP | NM001549.1 | IFIT4 |
| NM000235.1 | LIPA | NM003141.1 | SSA1 |
| NM000176.1 | NR3C1 | NM014705.1 | KIAA0716 |
| NM005737.2 | ARL7 | NM005197.1 | CHES1 |
| NM005737.2 | ARL7 | NM002907.1 | RECQL |
| BC001051.1 | ARL7 | U43328.1 | CRTL1 |
| NM006169.1 | NNMT | NM017925.1 | FLJ20686 |
| NM005862.1 | STAG1 | NM006773.2 | DDX18 |
| AI356412 | LYN | U20350.1 | CX3CR1 |
| NM002350.1 | LYN | NM005761.1 | PLXNC1 |
| BG107456 | TRIP-Br2 | NM004834.1 | MAP4K4 |
| NM021913.1 | AXL | NM021644.1 | HNRPH3 |
| NM002194.2 | INPP1 | NM006640.1 | MSF |
| NM019058.1 | RTP801 | NM004180.1 | TANK |
| NM002110.1 | HCK | AW148801 | NAP1L1 |
| NM030755.1 | TXNDC | AB011118.1 | KIAA0546 |
| NM030984.1 | TBXAS1 | AU145005 | SP3 |
| NM014350.1 | GG2-1 | N80918 | CG018 |
| BC001312.1 | P5 | BF439472 | ATP11A |
| U14990.1 | RPS3 | BE968801 | RPL35A |
| D83043.1 | HLA-B | AI985751 | NAP1L1 |
| AI888672 | NAP1L1 | AI735692 | LST1 |
| BC002387.1 | NAP1L1 | AA995910 | ALOX5 |
| M60334.1 | HLA-DRA | M12679.1 | HUMMHCW1A |

TABLE 1-continued

Genes With Up-Regulated Expression In stage I Renal Cell Carcinoma

| Genbank ID | Gene Symbol | Genbank ID | Gene Symbol |
|---|---|---|---|
| AF161522.1 | C3orf4 | AL133053.1 | FLJ23861 |
| BG256677 | IFI16 | X03348.1 | NR3C1 |
| M26880.1 | UBC | AC005339 | N/A |
| U17496.1 | PSMB8 | AK024836.1 | HLA-C |
| AF141347.1 | TUBA3 | AC003999 | SCAP2 |
| L01639.1 | CXCR4 | AJ224869 | CXCR4 |
| NM005445.1 | CSPG6 | AL022067 | PRDM1 |
| AB030655.1 | EFEMP2 | AL110158.1 | KIAA1078 |
| AF165520.1 | APOBEC3C | S81916.1 | N/A |
| AF009670.1 | ABCC3 | M80469 | N/A |
| AF020314.1 | CMRF-35H | NM002860.1 | PYCS |
| BC001606.1 | NCF2 | NM020198.1 | GK001 |
| BC005352.1 | GG2-1 | NM016304.1 | C15orf15 |
| AF281030.1 | HRIHFB2122 | AA102574 | BAZ1A |
| BC001052.1 | RECQL | NM024844.1 | PCNT1 |
| L32610.1 | HNRPH3 | NM015938.1 | CGI-07 |
| M23612.1 | RASA1 | NM018200.1 | HMG20A |
| AF109683.1 | LAIR1 | NM025235.1 | TNKS2 |
| BC002841.1 | HSA9761 | NM015991.1 | C1QA |
| D29640.1 | IQGAP1 | NM016090.1 | RBM7 |
| L25259.1 | CD86 | NM024554.1 | PGBD5 |
| M60333.1 | HLA-DRA | NM017718.1 | FLJ20220 |
| U13698.1 | CASP1 | NM017923.1 | FLJ20668 |
| U90940.1 | FCGR2C | NM030921.1 | DC42 |
| M90685.1 | HLA-G | BC004470.1 | ASC |
| M90684.1 | HLA-G | AK021413.1 | LARS |
| M90686.1 | HLA-G | BF444916 | FAD104 |
| L22453.1 | RPL3 | BC004819.1 | PLDN |
| U01351.1 | NR3C1 | AF247167.1 | AD031 |
| U62824.1 | HLA-C | U39402.1 | N/A |
| L07950.1 | HLA-B | BC006112.1 | DKFZP434B195 |
| AF348491.1 | CXCR4 | BG388615 | N/A |
| NM003079.1 | SMARCE1 | AB033007.1 | KIAA1181 |
| BE646386 | EXO70 | BG250721 | N/A |
| AI972475 | N/A | AK024221.1 | C40 |
| AA195999 | MAPK1 | BF477658 | N/A |
| AL049397.1 | N/A | BG251556 | KIAA1949 |
| BE895685 | KIAA0853 | AB033091.1 | KIAA1265 |
| M82882.1 | ELF1 | AK024350.1 | AMOTL1 |
| AB020633.1 | KIAA0826 | NM018440.1 | PAG |
| AL031781 | N/A | AW500180 | N/A |
| BF209337 | MGC4677 | AW026543 | N/A |
| AI709406 | N/A | AI092770 | N/A |
| AI806905 | N/A | NM020679.1 | AD023 |
| AI392933 | FLJ36090 | AK024855.1 | CTSS |
| AH42096 | N/A | AK000119.1 | N/A |
| AL137430.1 | N/A | AW977527 | PRDM1 |
| AV724266 | FLJ20093 | BE671060 | N/A |
| BF589359 | N/A | AL037450 | N/A |
| AW084125 | CAPZA1 | AI401535 | N/A |
| N20927 | RAP2B | AV683852 | N/A |
| AI627666 | LOC115548 | BF055144 | N/A |
| AV726322 | N/A | AA352113 | N/A |
| AI697657 | LANPL | BF056209 | N/A |
| BF002625 | N/A | X60592 | TMFRSF5 |
| BF439533 | N/A | | |

TABLE 2

Genes With Down-Regulated Expression In stage I Renal Cell Carcinoma

| Genbank ID | Gene Symbol | Genbank ID | Gene Symbol |
|---|---|---|---|
| L38487 | ESRRA | AK024386.1 | GRHPR |
| NM004415.1 | DSP | AL109716.2 | N/A |
| NM005327.1 | HADHSC | AK026411.1 | ALDOB |
| NM003321.1 | TUFM | M10943 | N/A |
| NM002084.1 | GPX3 | AW088547 | N/A |
| AI983043 | N/A | NM018049.1 | GNRPX |
| NM006066.1 | AKR1A1 | NM017900.1 | AKIP |
| NM006384.2 | CIB1 | NM006548.1 | IMP-2 |

TABLE 2-continued

Genes With Down-Regulated Expression In stage I Renal Cell Carcinoma

| Genbank ID | Gene Symbol | Genbank ID | Gene Symbol |
|---|---|---|---|
| NM001685.1 | ATP5J | NM025135.1 | KIAA1695 |
| NM014652.1 | IMP13 | NM016458.2 | LOC51236 |
| NM013410.1 | AK3 | NM022128.1 | RBSK |
| NM016725.1 | FOLR1 | NM015974.1 | CRYL1 |
| NM021151.1 | CROT | NM013333.1 | EPN1 |
| NM005951.1 | MT1H | AA133341 | C14orf87 |
| NM005952.1 | MT1X | AF226732.1 | NPD007 |
| AL080102.1 | N/A | AF265439.1 | MRPS15 |
| BC000931.2 | ATP5C1 | AI743534 | DKFZP564B1162 |
| BC005398.1 | DKFZP566D193 | AB042647.1 | B29 |
| D87292.1 | TST | AL522667 | ORF1-FL49 |
| AU151428 | IDH2 | BG255416 | KIAA0114 |
| BC000109.1 | ILVBL | AF308301.1 | MRPS26 |
| AF333388.1 | N/A | BE408081 | N/A |
| NM005953.1 | MT2A | AL521634 | FLJ32452 |
| BF217861 | N/A | BF203664 | MGC14288 |
| AA594937 | COBL | BE645551 | MGC39329 |
| AW052179 | COL4A5 | AW193698 | TGFBR3 |
| AI884867 | LOC155066 | BF540829 | N/A |
| BF246115 | N/A | W72455 | FLJ25476 |
| AW028110 | KIAA0500 | AI457453 | N/A |
| AW242315 | N/A | BF056892 | N/A |
| AW080549 | FUT3 | AK024386.1 | GRHPR |
| AW149846 | GPX3 | AL109716.2 | N/A |
| AI038402 | N/A | AA442776 | N/A |
| AI051046 | MGC4614 | AI913600 | N/A |
| AI659456 | N/A | AW771908 | N/A |
| AW664964 | N/A | AI807887 | N/A |
| AI631895 | SGK2 | AW102941 | N/A |
| AI263078 | FLJ31168 | AW024656 | N/A |
| BF057634 | HOXD8 | AB002342 | PRKWNK1 |
| AA746038 | GPR110 | | |

TABLE 3

Genes With Up-Regulated Expression In stage II Renal Cell Carcinoma

| Genbank ID | Gene Symbol | Genbank ID | Gene Symbol |
|---|---|---|---|
| NM006096.1 | NDRG1 | NM002053.1 | GBP1 |
| NM006096.1 | GNB2L1 | NM000089.1 | COL1A2 |
| NM001780.1 | CD63 | NM021105.1 | PLSCR1 |
| NM003118.1 | SPARC | NM002467.1 | MYC |
| NM000291.1 | PGK1 | NM001284.1 | AP3S1 |
| NM003870.1 | IQGAP1 | AI825926 | PLSCR1 |
| AB032261.1 | SCD | NM014736.1 | KIAA0101 |
| NM002629.1 | PGAM1 | AF161461.1 | LEPROTL1 |
| NM003564.1 | TAGLN2 | NM014873.1 | KIAA0205 |
| NM000310.1 | PPT1 | AI005043 | N/A |
| NM003405.1 | YWHAH | NM000416.1 | IFNGR1 |
| U82164.1 | MIC2 | NM004172.1 | SLC1A3 |
| NM002305.2 | LGALS1 | NM004207.1 | SLC16A3 |
| NM001096.1 | ACLY | AI761561 | HK2 |
| NM002121.1 | HLA-DPB1 | Y09216.1 | N/A |
| NM021038.1 | MBNL | NM002922.1 | RGS1 |
| NM003651.1 | CSDA | NM005990.1 | STK10 |
| AV685920 | CAPZA2 | NM014863.1 | GALNAC4S-6ST |
| NM002654.1 | PKM2 | NM014737.1 | RASSF2 |
| NM001175.1 | ARHGDIB | NM000418.1 | IL4R |
| BC000182.1 | ANXA4 | BC000658.1 | STC2 |
| NM001153.2 | ANXA4 | NM003751.1 | EIF3S9 |
| NM001975.1 | ENO2 | NM002339.1 | LSP1 |
| NM006435.1 | IFTTM2 | NM004604.1 | STX4A |
| NM001387.1 | DPYSL3 | NM006404.1 | PROCR |
| BG398414 | RPA1 | AF275945.1 | EVA1 |
| NM004039.1 | ANXA2 | NM004221.1 | NK4 |
| NM005534.1 | IFNGR2 | NM004556.1 | NFKBIE |
| AL136877.1 | SMC4L1 | NM004688.1 | NMI |
| NM014876.1 | KIAA0063 | NM003332.1 | TYROBP |
| NM024830.1 | FLJ12443 | NM015136.1 | STAB1 |
| NM005505.1 | SCARB1 | NM006019.1 | TCIRG1 |

TABLE 3-continued

Genes With Up-Regulated Expression In stage II Renal Cell Carcinoma

| Genbank ID | Gene Symbol | Genbank ID | Gene Symbol |
|---|---|---|---|
| NM003025.1 | SH3GL1 | NM004877.1 | GMFG |
| NM013285.1 | HUMAUANTIG | NM002317.1 | LOX |
| NM005720.1 | ARPC1B | NM025201.1 | PP1628 |
| AW157070 | EGFR | NM014800.1 | ELMO1 |
| NM002835.1 | PTPN12 | L41944.1 | IFNAR2 |
| NM004428.1 | EFNA1 | NM007268.1 | Z39IG |
| AW006290 | SUDD | NM006994.2 | BTN3A3 |
| NM014791.1 | MELK | AF091352.1 | VEGF |
| NM014882.1 | KIAA0053 | AB035482.1 | ICB-1 |
| NM003864.1 | SAP30 | Z24727.1 | TPM1 |
| NM001558.1 | IL10RA | M19267.1 | TPM1 |
| NM003264.1 | TLR2 | U13700.1 | CASP1 |
| NM014221.1 | MTCP1 | M27281.1 | VEGF |
| AV756141 | CSF2RB | BC005838.1 | N/A |
| AI123251 | LCP2 | BC005858.1 | FN1 |
| NM006433.2 | GNLY | BC005926.1 | EVI2B |
| NM000861.2 | HRH1 | BE513104 | YARS |
| NM001870.1 | CPA3 | AU147399 | CAV1 |
| NM003586.1 | DOC2A | AK023154.1 | HN1L |
| NM004271.1 | MD-1 | AK021757.1 | KIAA0648 |
| NM014932.1 | NLGN1 | H95344 | VEGF |
| NM014947.1 | KIAA1041 | AB023231.1 | FNBP4 |
| NM000647.2 | CCR2 | AL523076 | N/A |
| NM002562.1 | P2RX7 | NM030666.1 | SERPINB1 |
| NM006058.1 | TNIP1 | AB018289.1 | KIAA0746 |
| NM013447.1 | EMR2 | AW043713 | SULF1 |
| NM013416.1 | NCF4 | BE880591 | EP400 |
| NM001776.1 | ENTPD1 | AU158495 | NOTCH2 |
| NM020037.1 | ABCC3 | BE965029 | N/A |
| NM006135.1 | CAPZA1 | AL564683 | CEBPB |
| NM007036.2 | ESM1 | AA349595 | RAB6IP1 |
| AF034607.1 | CLIC1 | AI809341 | PTPRC |
| BC000915.1 | PDLIM1 | AW205215 | KIAA0286 |
| AL162068.1 | NAP1L1 | BE349017 | HA-1 |
| NM006947.1 | SRP72 | AF070592.1 | HSKM-B |
| L12387.1 | SRI | AI769685 | CARS |
| AF141349.1 | N/A | AI935123 | LOC113146 |
| AF263293.1 | SH3GLB1 | BG255188 | N/A |
| BC000389.1 | TM4SF7 | AI088622 | PRKCDBP |
| AF007162.1 | CRYAB | BE222709 | N/A |
| D38616.1 | PHKA2 | AW007573 | DKFZP586L151 |
| AV717590 | ENTPD1 | BG332462 | N/A |
| U87967.1 | ENTPD1 | AI862658 | FEM1C |
| H23979 | MOX2 | AI934469 | KIAA0779 |
| AF063591.1 | MOX2 | AB018345.1 | KIAA0802 |
| BC005254.1 | CLECSF2 | W87466 | LOC92689 |
| BC000893.1 | H2BFT | BE908217 | ANXA2 |
| L22431.1 | VLDLR | NM005615.1 | RNASE6 |
| AI741056 | SELPLG | BE300252 | K-ALPHA-1 |
| AF084462.1 | RIT1 | BF740152 | MYO1F |
| U62027.1 | C3AR1 | AV711904 | LYZ |
| M87507.1 | CASP1 | AW072388 | N/A |
| J04132.1 | CD3Z | AW190316 | SHMT2 |
| M31159.1 | IGFBP3 | NM005412.1 | SHMT2 |
| AF257318.1 | SH3GLB1 | NM006417.1 | IFI44 |
| BC001388.1 | ANXA2 | AL008730 | C6orf4 |
| AF130095.1 | FN1 | L16895 | LOC114990 |
| AF022375.1 | VEGF | Z21533.1 | HHEX |
| AA807529 | MCM5 | AK022955.1 | DKFzp762L0311 |
| AK026737.1 | FN1 | BF001267 | N/A |
| X14355.1 | N/A | AL558987 | N/A |
| AK025608.1 | KIAA0930 | AA577672 | LOC151636 |
| AF183421.1 | RAB31 | BE620734 | ZAK |
| NM002695.1 | POLR2E | AI937446 | N/A |
| AF288391.1 | C1orf24 | H99792 | N/A |
| NM003730.2 | RNASE6PL | BE966748 | N/A |
| NM016359.1 | ANKT | AI659418 | MGC21854 |
| NM014164.2 | FXYD5 | AI990891 | DKFzp761K2222 |
| NM022736.1 | FLJ14153 | AA827892 | N/A |
| NM021158.1 | C20orf97 | AL135264 | N/A |
| NM017792.1 | FLJ20373 | AI375753 | N/A |
| NM020142.1 | LOC56901 | AA573502 | TAP2 |
| NM016448.1 | RAMP | BG387557 | CASP2 |
| NM005767.1 | P2Y5 | AA554833 | MAP1B |
| NM020169.1 | LXN | AK026764.1 | N/A |
| NM022834.1 | FLJ22215 | AU146532 | PDK1 |
| NM018460.1 | BM046 | BE348597 | N/A |
| NM024629.1 | FLJ23468 | AL577758 | LOC133957 |
| NM018641.1 | C4S-2 | AI133452 | FGG |
| NM018295.1 | FLJ11000 | AU157224 | N/A |
| NM024576.1 | FLJ21079 | AI742057 | N/A |
| NM016582.1 | PHT2 | BE500942 | N/A |
| NM003116.1 | SPAG4 | N25631 | RFXANK |
| NM018454.1 | ANKT | AU145366 | N/A |
| NM018099.1 | FLJ10462 | AW270037 | KIAA0779 |
| NM007072.1 | HHLA2 | BF526978 | N/A |
| NM022445.1 | TPK1 | AW182575 | N/A |
| AW173623 | TDE1 | BF339831 | MGC13114 |
| AB044088.1 | BHLHB3 | AI056992 | N/A |
| AF043244.1 | NOL3 | BE222668 | N/A |
| AF133207.1 | H11 | BG165011 | N/A |
| AF313468.1 | CLECSF12 | AI188445 | MGC14289 |
| AA191576 | NPM1 | BE551416 | HAK |
| AI765383 | KIAA1466 | AI972498 | a1/3GTP |
| BC003654.1 | SLC27A3 | AW662189 | N/A |
| W60806 | N/A | AA142842 | N/A |
| AI335263 | NETO2 | BF939473 | N/A |
| AI378406 | EGLN3 | AI681260 | N/A |
| BC005400.1 | FKSG14 | AA551090 | AP1S2 |
| AI761520 | CENTA2 | AA045175 | MS4A6A |
| BC000771.1 | TPM3 | W05495 | N/A |
| BC000190.1 | HSPC216 | AI093231 | N/A |
| BC002776.1 | SEMA5B | AI565054 | N/A |
| AF132203.1 | SCD | AL553774 | N/A |
| BC006107.1 | ARHGAP9 | AK023470.1 | MGC15875 |
| AK024263.1 | N/A | AL157377 | ENPP3 |
| AK024846.1 | SET7 | AL139109 | TEX11 |
| BE878463 | N/A | AK025631.1 | POLH |
| AW304786 | PTR4 | AI873425 | N/A |
| AI769269 | N/A | BF541967 | N/A |
| AI935334 | N/A | AI686890 | N/A |
| BF437747 | SAMHD1 | AI936034 | ITGA4 |
| AW300953 | N/A | U88964 | ISG20 |
| H37811 | N/A | AJ243797 | TREX1 |
| AA603344 | SAMHD1 | D29642 | KIAA0053 |
| AA742310 | N/A | D87433 | STAB1 |
| AI248208 | FLJ25804 | AI129310 | FLJ21562 |
| AI962367 | ECGF1 | | |

TABLE 4

Genes With Down-Regulated Expression In stage II Renal Cell Carcinoma

| Genbank ID | Gene Symbol | Genbank ID | Gene Symbol |
|---|---|---|---|
| NM012248.1 | SPS2 | AB019695.1 | TXNRD2 |
| NM002300.1 | LDHB | M61900.1 | PTGDS |
| BC000306.1 | HADHSC | BF967998 | N/A |
| NM001640.2 | APEH | BF967998 | N/A |
| NM005875.1 | GC20 | AL526243 | KIAA0446 |
| NM003365.1 | UQCRC1 | NM000532.1 | PCCB |
| BF031714 | HYA22 | BE042354 | LDHB |
| NM005808.1 | HYA22 | AI587323 | ATP5A1 |
| AF113129.1 | ATP6V1A1 | AW195882 | ATPW |
| NM002402.1 | MEST | H71135 | ADH6 |
| NM006844.1 | ILVBL | AV659180 | ALDOB |
| NM006434.1 | SEMA3B | AK027006.1 | TNRC9 |
| NM002496.1 | NDUFS8 | AV693216 | PLXNB1 |
| NM006556.1 | PMVK | BG398937 | N/A |
| NM004255.1 | COX5A | NM002489.1 | NDUFA4 |
| NM002225.2 | IVD | NM003849.1 | SUCLG1 |
| NM004524.1 | LLGL2 | NM014019.1 | HSPC009 |
| AI950380 | BCL7A | NM024952.1 | FLJ20950 |
| AB020707.1 | WASF3 | NM014185.1 | MOG1 |
| NM000481.1 | AMT | NM018013.1 | FLJ10159 |
| NM012317.1 | LDOC1 | NM018373.1 | SYNJ2BP |

TABLE 4-continued

Genes With Down-Regulated Expression In stage II Renal Cell Carcinoma

| Genbank ID | Gene Symbol | Genbank ID | Gene Symbol |
|---|---|---|---|
| NM006456.1 | STHM | NM014067.2 | LRP16 |
| NM006614.1 | CHL1 | NM013261.1 | PPARGC1 |
| NM015393.1 | DKFZP564O0823 | NM021963.1 | NAP1L2 |
| AV729634 | DNAJC6 | NM018658.1 | KCNJ16 |
| NM002628.1 | PFN2 | NM014553.1 | LBP-9 |
| NM003500.1 | ACOX2 | AF112204.1 | ATP6V1H |
| NM002655.1 | PLAG1 | AU145941 | CDC14B |
| NM004393.1 | DAG1 | AF061264.1 | MGC4825 |
| NM003026.1 | SH3GL2 | BF941492 | FLJ10496 |
| NM002010.1 | FGF9 | AI984229 | HSPC121 |
| NM014033.1 | DKFZP586A0522 | N71923 | FLRT3 |
| NM004868.1 | GPSN2 | BC005050.1 | NICN1 |
| BC000649.1 | UQCRFS1 | AF172327.1 | N/A |
| S69189.1 | ACOX1 | AF356515.1 | HINT2 |
| AF153330.1 | SLC19A2 | BE620739 | RHOBTB3 |
| AF094518.1 | ESRRG | BF435123 | N/A |
| M55575.1 | BCKDHB | AW149498 | BTBD6 |
| BE044480 | MGC32124 | AW024437 | LOC118491 |
| BF382393 | N/A | AW195353 | N/A |
| AV751731 | PNKP | BE044193 | N/A |
| U55984 | N/A | AI493303 | FLJ31709 |
| BF059512 | DNER | AI636080 | N/A |
| AK025934.1 | Evi1 | BF509031 | ATP6V1G3 |
| AL036088 | SEMA6D | AW242920 | N/A |
| BE964222 | FLJ38482 | BF002046 | ANGPTL1 |
| AW290940 | N/A | BF130943 | N/A |
| AL545998 | N/A | AW452631 | N/A |
| AW274874 | N/A | AI792937 | N/A |
| AI709389 | N/A | AI810572 | N/A |
| BF224092 | MGC15854 | BG165743 | LOC112817 |
| AU145805 | N/A | AW466989 | N/A |
| AW079843 | MGC33338 | R48991 | N/A |
| AW138815 | N/A | BF029215 | MSI2 |
| AW242286 | N/A | D21851 | LARS2 |
| AW025023 | N/A | Z83838 | ARHGAP8 |
| BE672659 | N/A | | |

TABLE 5

Genes With Up-Regulated Expression In both stage I & stage II Renal Cell Carcinoma

| Genbank ID | Gene Symbol | Genbank ID | Gene Symbol |
|---|---|---|---|
| NM005566.1 | LDHA | NM014812.1 | KIAA0470 |
| NM000291.1 | PGK1 | AF208043.1 | IFI16 |
| NM001219.2 | CALU | BC002654.1 | TUBB-5 |
| NM002966.1 | S100A10 | BC006379.1 | K-ALPHA-1 |
| NM000034.1 | ALDOA | BC006481.1 | K-ALPHA-1 |
| NM002627.1 | PFKP | AF000426.1 | LST1 |
| NM006082.1 | K-ALPHA-1 | AF000424.1 | LST1 |
| AI922599 | VIM | BG500301 | ITGB1 |
| NM020474.2 | GALNT1 | AL516350 | ARPC5 |
| NM006406.1 | PRDX4 | M27487.1 | HLA-DPA1 |
| NM015344.1 | LEPROTL1 | M27487.1 | HLA-DPA1 |
| NM014755.1 | TRIP-Br2 | AW517686 | ATP2B4 |
| AI796269 | NBS1 | AL581768 | K-ALPHA-1 |
| NM005783.1 | APACD | AA524505 | TSGA |
| BF197655 | N/A | Z78330 | ACTR3 |
| NM001233.1 | CAV2 | Z78330 | ACTR3 |
| NM002845.1 | PTPRM | BG532690 | ITGA4 |
| NM014302.1 | SEC61G | AW005535 | RAP2B |
| U47924 | CD4 | NM007161.1 | LST1 |
| NM004106.1 | FCER1G | AK026577.1 | ALDOA |
| NM015474.1 | SAMHD1 | AI091079 | SHC1 |
| NM004915.2 | ABCG1 | AV713720 | LST1 |
| NM002432.1 | MNDA | NM021103.1 | TMSB10 |
| NM005565.2 | LCP2 | NM016337.1 | RNB6 |
| NM005531.1 | IFI16 | NM013260.1 | HCNGP |
| NM005849.1 | IGSF6 | NM021199.1 | SQRDL |
| NM002189.1 | IL15RA | NM018149.1 | FLJ10587 |
| NM004353.1 | SERPINH1 | NM016951.2 | CKLF1 |

TABLE 5-continued

Genes With Up-Regulated Expression In both stage I & stage II Renal Cell Carcinoma

| Genbank ID | Gene Symbol | Genbank ID | Gene Symbol |
|---|---|---|---|
| NM017760.1 | FLJ20311 | AB033038.1 | FLJ10392 |
| NM022349.1 | MS4A6A | AI184968 | C1QG |
| NM023003.1 | TM6SF1 | AL161725 | FLJ00026 |
| NM016184.1 | CLECSF6 | NM018440.1 | PAG |
| NM031284.1 | DKFZP434B195 | AL553942 | FLJ31951 |
| BC002342.1 | CORO1C | AI394438 | N/A |
| AA775177 | PTPRE | T64884 | N/A |
| AL162070.1 | CORO1C | T64884 | N/A |
| AF253977.1 | MS4A6A | AW511319 | N/A |
| AF237908.1 | MS4A6A | AI640834 | RA-GEF-2 |
| W03103 | DDEF1 | AI655467 | N/A |
| AK022888.1 | FENS-1 | AL161725 | FLJ00026 |
| AI141784 | N/A | T92908 | N/A |

TABLE 6

Genes With Down-Regulated Expression In Both stage I And stage II Renal Cell Carcinoma

| Genbank ID | Gene Symbol | Genbank ID | Gene Symbol |
|---|---|---|---|
| NM004092.2 | ECHS1 | BC002449.1 | FLJ13612 |
| NM000270.1 | NP | J02639.1 | SERPINA5 |
| NM002354.1 | TACSTD1 | BC002571.1 | DKFZP564O243 |
| AF017987.1 | SFRP1 | U03884.1 | KCNJ1 |
| NM003012.2 | SFRP1 | AF173154.1 | HYAL1 |
| NM000666.1 | ACY1 | AF130103.1 | PBP |
| NM000191.1 | HMGCL | AL117618.1 | PDHB |
| NM015254.1 | KIF13B | AF063606.1 | N/A |
| NM000140.1 | FECH | BC005314.1 | N/A |
| U75667.1 | ARG2 | BF686267 | PBP |
| NM000196.1 | HSD11B2 | AI742553 | PRKWNK1 |
| NM014636.1 | RALGPS1A | D83782.1 | SCAP |
| NM001441.1 | FAAH | AB029031.1 | TBC1D1 |
| NM005978.2 | S100A2 | AK025432.1 | KIAA0564 |
| NM001678.1 | ATP1B2 | AL117643.1 | N/A |
| NM001099.2 | ACPP | AW772192 | N/A |
| NM014731.1 | ProSAPiP1 | NM003944.1 | SELENBP1 |
| BF343007 | N/A | AL049977.1 | CLDN8 |
| NM000035.1 | ALDOB | AK023937.1 | THEA |
| NM005950.1 | MT1G | AK025084.1 | TNRC9 |
| NM002371.2 | MAL | X03363.1 | ERBB2 |
| NM006984.1 | CLDN10 | AK026411.1 | ALDOB |
| NM002567.1 | PBP | NM016026.1 | RDH11 |
| NM000019.1 | ACAT1 | NM016286.1 | DCXR |
| NM001692.1 | ATP6V1B1 | NM019027.1 | FLJ20273 |
| X77737.1 | N/A | BG338251 | RAB7L1 |
| NM006226.1 | PLCL1 | NM006113.2 | VAV3 |
| NM000893.1 | KNG | NM018075.1 | FLJ10375 |
| NM000412.2 | HRG | NM013271.1 | PCSK1N |
| NM001963.2 | EGF | NM017586.1 | C9orf7 |
| NM003361.1 | UMOD | NM016321.1 | RHCG |
| NM000050.1 | ASS | NM025247.1 | MGC5601 |
| NM001438.1 | ESRRG | BC002449.1 | FLJ13612 |
| NM020632.1 | ATP6V0A4 | AI379517 | N/A |
| AI632015 | SLC12A1 | AA058832 | MGC33926 |
| NM000701.1 | ATP1A1 | AW274034 | N/A |
| NM031305.1 | DKFZP564B1162 | AI580268 | NUDT6 |
| AF130089.1 | ALDH6A1 | AI761947 | DKFZP564B1162 |
| AK025651.1 | N/A | AI793201 | N/A |
| W45551 | MMP24 | AK025898.1 | N/A |
| W67995 | FXC1 | AB046810.1 | C20orf23 |
| AL136566.1 | IBA2 | AK024204.1 | N/A |
| AF105366.1 | SLC12A6 | BF594722 | N/A |
| AF284225.1 | DMRT2 | R88990 | N/A |
| AA191708 | N/A | N73742 | N/A |
| AL355708.1 | N/A | AI697028 | FLJ90165 |
| BE783949 | FLJ10101 | BF590528 | N/A |
| AL529672 | N/A | AI733359 | N/A |
| AL568674 | MYBBP1A | H20179 | N/A |
| AU147564 | CLMN | AA991551 | MGC14839 |
| AK000208.1 | N/A | AI758950 | SLC26A7 |

TABLE 6-continued

Genes With Down-Regulated Expression In Both stage I And stage II Renal Cell Carcinoma

| Genbank ID | Gene Symbol | Genbank ID | Gene Symbol |
|---|---|---|---|
| AB051536.1 | FLJ14957 | AA911561 | N/A |
| AI569747 | TFDP2 | AI769774 | N/A |
| AK025562.1 | N/A | AA669135 | N/A |
| AI660243 | TMPRSS2 | AW136060 | SLC13A2 |
| N50413 | N/A | AI733593 | N/A |
| AI347918 | N/A | BF739841 | N/A |
| AL536553 | GRP58 | AA600175 | N/A |
| BC000282.1 | LOC89894 | BF477980 | N/A |
| BF106962 | FAM3B | AI934557 | N/A |
| AI051248 | FLJ32115 | BE326951 | KNG |
| AI928242 | N/A | AI632567 | N/A |
| BG236006 | N/A | BE300882 | N/A |
| AI653107 | N/A | BE855713 | N/A |
| AI824037 | FLJ25461 | AA485440 | DBP |
| R61322 | N/A | AA915989 | FLJ10743 |
| AW071744 | KCNJ10 | AA085764 | SIGIRR |
| BF059276 | N/A | | |

EXAMPLE 6

Figure 11A:
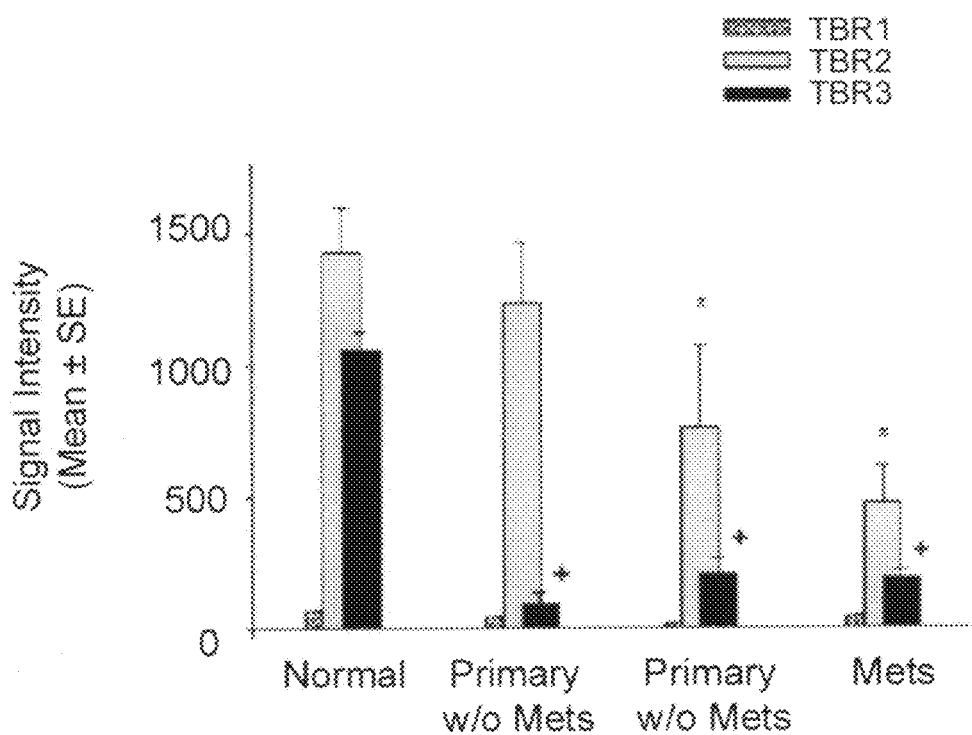
FIGS. 11A-11B show stepwise loss of type III αreceptor (TBR3) and type II TGF-β receptor (TBR2) mRNA expression during renal cell carcinogenesis and progression in patient tissue samples.

Loss of TGF-β Receptor Expression Demonstrated by Gene Array and Real-Time PCR in Renal Cell Carcinoma Expression of type I TGF-β receptor (TBR1), type II TGF-β receptor (TBR2), and type III TGF-β receptor (TBR3) mRNA were compared in normal renal tissue, primary renal cell carcinoma without metastasis, primary lesions of metastatic renal cell carcinoma, and metastatic lesions. A summary of gene array analysis was presented as average signal intensities in FIG. 11A (mean±standard error). The signal intensity for TBR1 (cross-hatched bars) was relatively low, although TBR1 was scored as 'Present' in all samples. No significant changes in TBR1 expression were observed. TBR2 (gray bars) was abundantly expressed in normal epithelium and in primary lesions of nonmetastatic renal cell carcinoma. TBR2 was significantly reduced in primary lesions with metastatic disease (P<0.028 by ANOVA). TBR2 was even more reduced in metastatic lesions. TBR3 expression was high in normal epithelium, but was significantly reduced in each of the five primary tumors with nonmetastatic disease (black bars). TBR3 expression was also reduced in primary tumors with metastatic lesions and in metastatic lesions themselves.

Figure 11B:
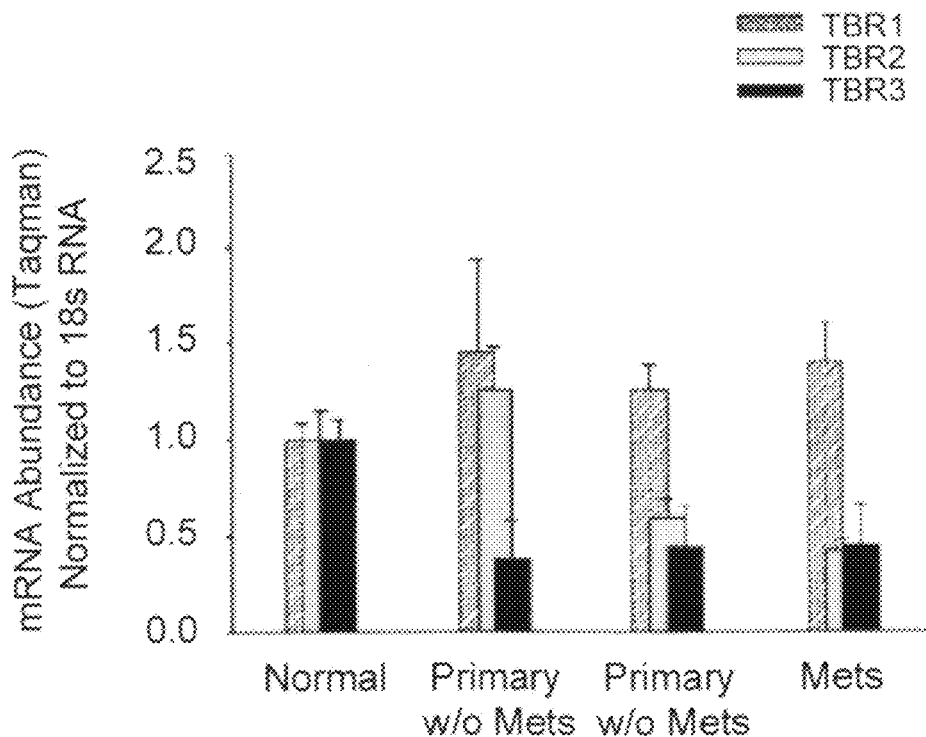

These expression patterns were confirmed by real-time PCR (Tagman®) in the 10 patients used for gene array analysis. Means and standard errors for individual samples are shown in FIG. 11B. All data were normalized to 18S rRNA and calibrated to target abundance in the paired normal tissues. TBR1 mRNA abundance did not change (cross-hatched bars), consistent with the gene chip data. TBR2 (gray bars) was not reduced in primary tumors without metastases, whereas TBR2 was significantly reduced in primary tumors with metastatic disease and in metastatic lesions. TBR3 was reduced in all tumors (black bars).

The investigators have subsequently completed real-time PCR analysis of TBR1, TBR2, and TBR3 expression in 16 primary tumors without metastases (plus paired normal epithelium) and nine samples of primary tumors with metastatic disease, paired metastatic lesions, and paired normal tissue. The data were consistent with those shown for the samples analyzed in FIG. 11A. TBR3 expression was significantly reduced in all tumors; whereas TBR2 expression was reduced in only 1/16 primary tumors without metastatic lesions, but was reduced in primary tumors with metastatic lesions (8/9). These data show that loss of TBR3 is an early event in renal cell carcinoma, strongly suggesting that TBR3 plays a critical role in renal cell carcinoma carcinogenesis.

The loss of TBR3 mRNA expression was also correlated with TNM scores (T, histological score; N, lymph node number; M, number of organ metastases) from patient samples (data not shown). TBR3 mRNA expression was suppressed in the earliest stage, stage I, and was found to be suppressed in all tumor stages (I-IV). In addition, loss of TBR2 in the primary tumor is significantly associated with acquisition of the metastatic phenotype and clinically manifests as metastatic progression.

EXAMPLE 7

Attenuation of TGF-β-Mediated Signal Transduction in Human Renal Cell Carcinoma

Figure 12:
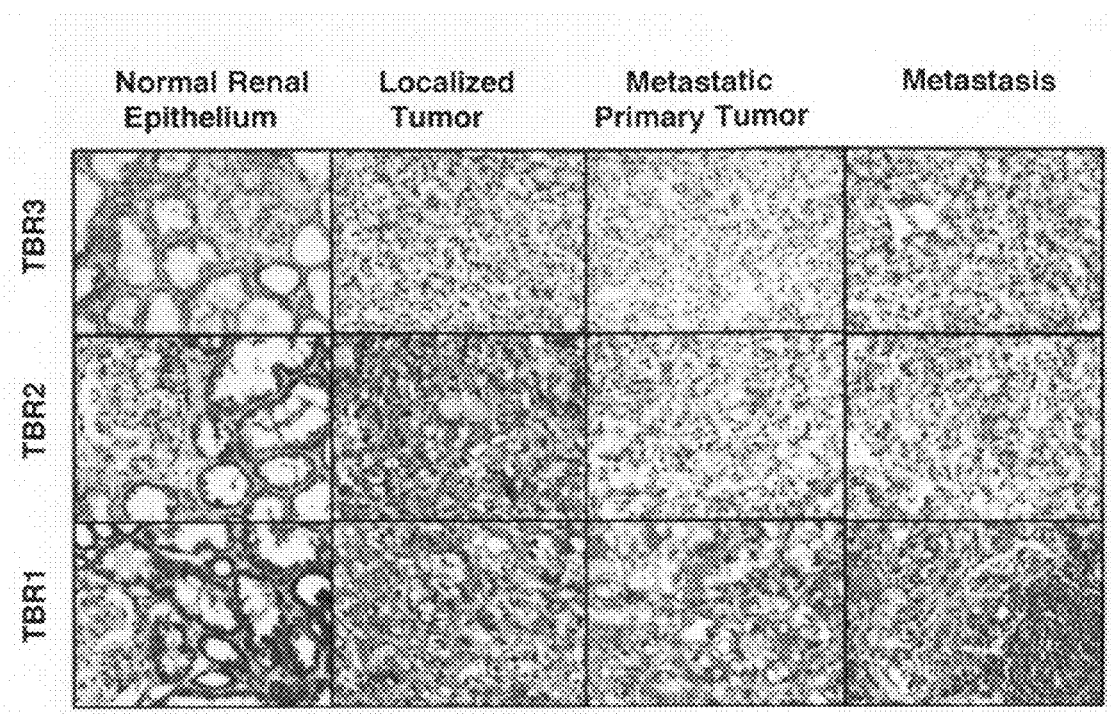
FIG. 12 shows immunohistochemistry of patient tissue demonstrating loss of type III αreceptor (TBR3) expression (top row) in all tumors, loss of type II αreceptor (TBR2) expression (middle row) in patients diagnosed with metastatic tumors, and no change in type I αreceptor (TBR1) protein expression (bottom row).

Decreased type III TGF-β receptor (TBR3) mRNA expression in all tumors was associated with failure to detect TBR3 protein by immunohistochemistry (FIG. 12). Type I TGF-β receptor (TBR2) protein was detected in localized tumor (primary, no mets), but was not detectable in primary tumors with metastatic disease or in corresponding metastatic lesions. Type I TGF-β receptor (TBR1) protein was detected in normal tissue and in all tumor samples.

Figure 13:
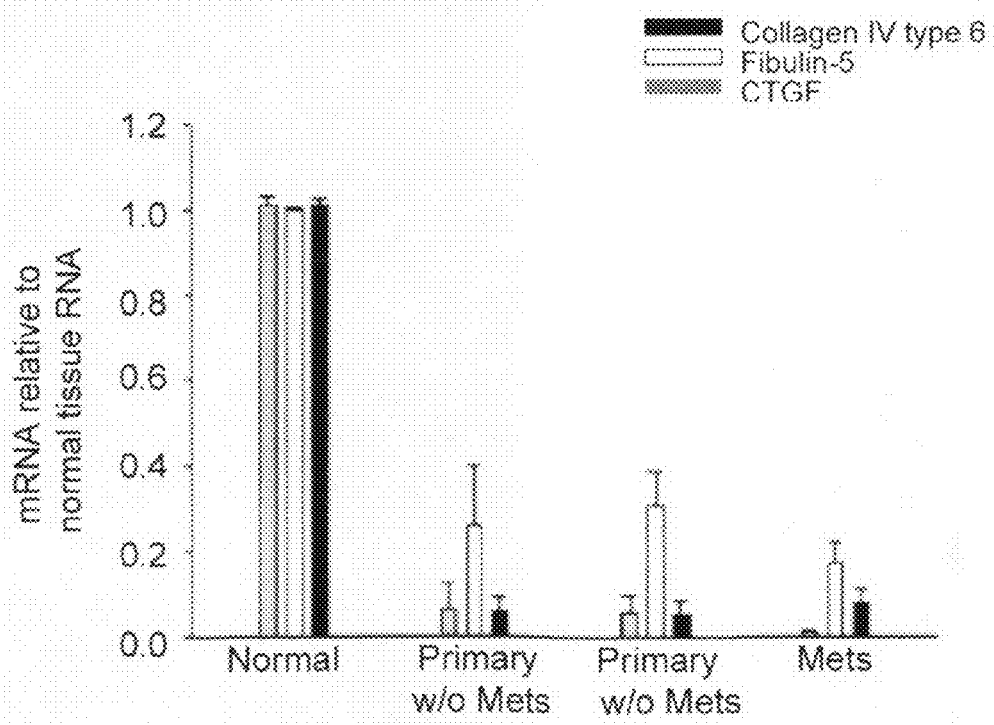
FIG. 13 demonstrates down-regulation of TGF-β-regulated genes in human tumor tissues by real-time PCR. Genes known to be up-regulated by α are suppressed in tumor tissues. Down-regulation of collagen IV type 6, fibulin 5, and connective tissue growth factor (CTGF) mRNA in tumor tissues were compared to matched normal tissue controls. Values were normalized to 18 s mRNA. Each matching tumor value was compared to its respective normal control. The mean±s.d. was calculated for each sample group with n values of 10-15 matched samples.

The investigators hypothesized that these losses seen in TGF-β receptor expression would manifest as an attenuation of TGF-β mediated signal transduction, and would significantly alter the expression of TGF-β regulated genes. From the gene array data disclosed above, 13 known TGF-β/Smad-regulated genes were down-regulated in renal cell carcinoma (Table 7). Using mRNA from 35 patient-matched samples, the investigators verified loss of expression of three of these genes by comparing matched normal and tumor tissue. Real-time PCR was used to measure the expression of Collagen IV type 6, fibulin-5, and connective-tissue growth factor (CTGF). Collagen IV type 6 (gray bars) is an extracellular matrix protein that plays a critical role in the regulation of membrane integrity and cell signaling. Fibulin-5 is a recently discovered TGF-β-regulated gene, which has tumor suppressor activity. Fibulin-5 is an extracellular matrix protein that is believed to signal through interaction with integrins. CTGF is a secreted protein involved in angiogenesis, skeletogenesis, and wound healing. CTGF enhances TGF-β1 binding to TBR2, and CTGF and TGF-β collaborate to regulate the expression of extracellular matrix proteins during renal fibrosis. As summarized graphically in FIG. 13, all the evaluated TGF-β-regulated genes were down-regulated in early tumor stages, suggesting that renal cell carcinoma undergoes loss of TGF-β responsiveness at an early stage. These data indicate that this loss of TGF-β sensitivity is due, primarily, to loss of type III TGF-β receptor (TBR3) in early tumor development and further loss of sensitivity in metastatic disease is mediated through subsequent loss of type II TGF-β receptor (TBR2).

TABLE 7

Known TGF-β-Regulated Genes Found To Be Down-Regulated
In Localized Tumors By Gene Array Analysis

| GenBank No. | Gene Name | Fold Attenuation |
|---|---|---|
| S81439 | TGFβ-induced early growth factor (TIEG) | 2.5 |
| AF093118 | Fibulin 5 | 4.0 |
| U42408 | Ladinin 1 | 15.4 |
| U01244 | Fibulin 1 | 4.8 |
| J05257 | Dipeptidase 1 | 7.7 |
| D21337 | Collagen, type IV, a6 | 3.6 |
| X80031 | Collagen, type IV, a3 | 2.4 |
| M64108 | Collagen, type XIV, a1 | 3.2 |
| M98399 | Collagen, type I receptor | 4.2 |
| L23808 | Matrix metallo-proteinase 12 | 3.7 |
| M35999 | Integrin, b3 | 2.5 |
| AI304854 | $p27^{Kip1}$ | 2.1 |
| J05581 | Mucin 1 | 6.5 |

Data were analysed by a combination of two-dimensional ANOVA, Affymetrix MAS5.0, and hierarchical cluster analysis using Spotfire to identify genes that are down-regulated in local tumors versus that of normal renal cortex tissue.

EXAMPLE 8

TGF-β Receptor Expression in Renal Cell Carcinoma Cell Lines

Figure 14A:
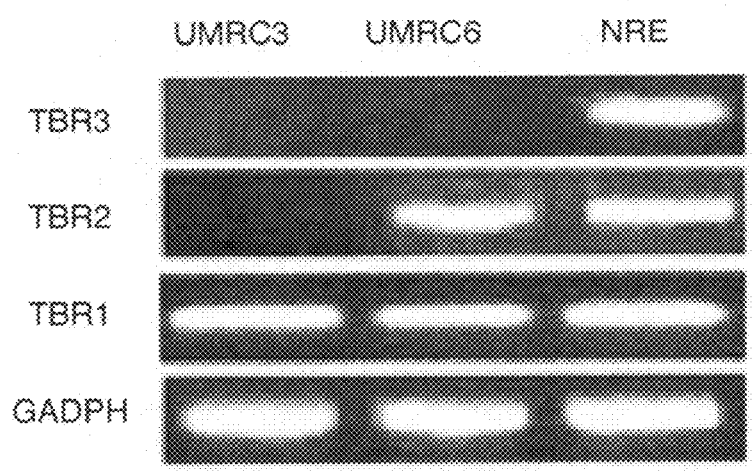
FIGS. 14A-14B show tumor cell lines that lose type III αreceptor (TBR3) and type I TGF-β receptor (TBR2) expression.
Figure 14B:
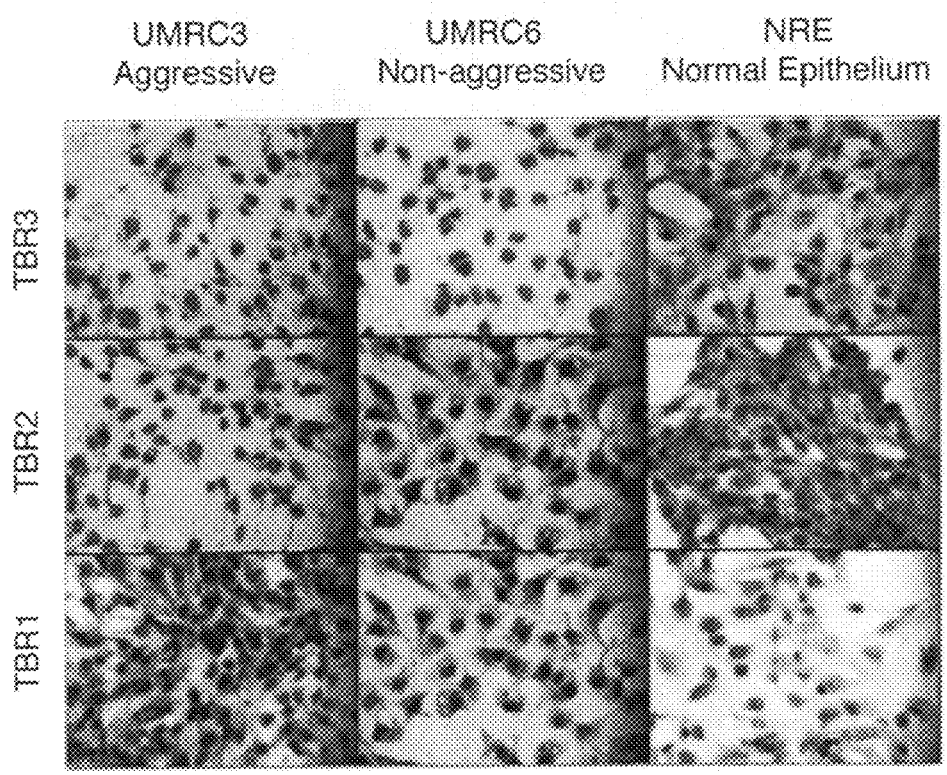

Human renal cell carcinoma cell lines were identified that recapitulate the clinical observations of TGF-β receptor biology described above. UMRC6 cells were derived from a clinically localized human renal cell carcinoma (Grossman et al., 1985). As shown in FIG. 14A, UMRC6 cells express type II TGF-β receptor (TBR2) mRNA, but not type III TGF-β receptor (TBR3). Immunohistochemical analysis (FIG. 14B) confirms the presence of TBR2 protein and the absence of TBR3 expression. UMRC3 cells were derived from the primary tumor of a patient with metastatic renal cell carcinoma. This highly aggressive cell line lacks detectable TBR2 and TBR3 mRNA (FIG. 14A) and protein (FIG. 14B).

In addition to these relevant laboratory models, normal renal epithelial (NRE) tissue was harvested from nephrectomy specimens and established as primary cultures (Trifillis, 1999). As shown in FIGS. 14A and 14B, these primary cultures of NRE expressed TBR3, TBR2, and TBR1 mRNA and protein in vitro. NRE cells can be grown in culture for 10 passages and were easily isolated and characterized. NRE cells were characterized for cytokeratin expression and tubule-specific gene expression, for example, megalin (data not shown). Thus, there are relevant cell models in which TBR2 and TBR3 expression can be manipulated to examine the impact of TGF-β receptor biology on the carcinogenesis and progression of human renal cell carcinoma in vitro.

EXAMPLE 9

TGF-β Activity in Renal Cell Carcinoma Cell Lines

It is well known that TGF-β1 inhibits cell proliferation in epithelial cells. The present example demonstrates the effects of TGF-β on renal tumor cell proliferation.

DNA content of cells was used as a measure of cell proliferation. Cells were plated at 20,000 cells/well in 12-well plates. Cells were grown in 10% FBS:DMEM:penicillin: streptomycin. The following day, media were exchanged with appropriate treatment added to the media. On day 3 of treatment, cells were analyzed for DNA content using Hoechst reagent. DNA standard was used to correlate DNA content per well.

Figure 15A:
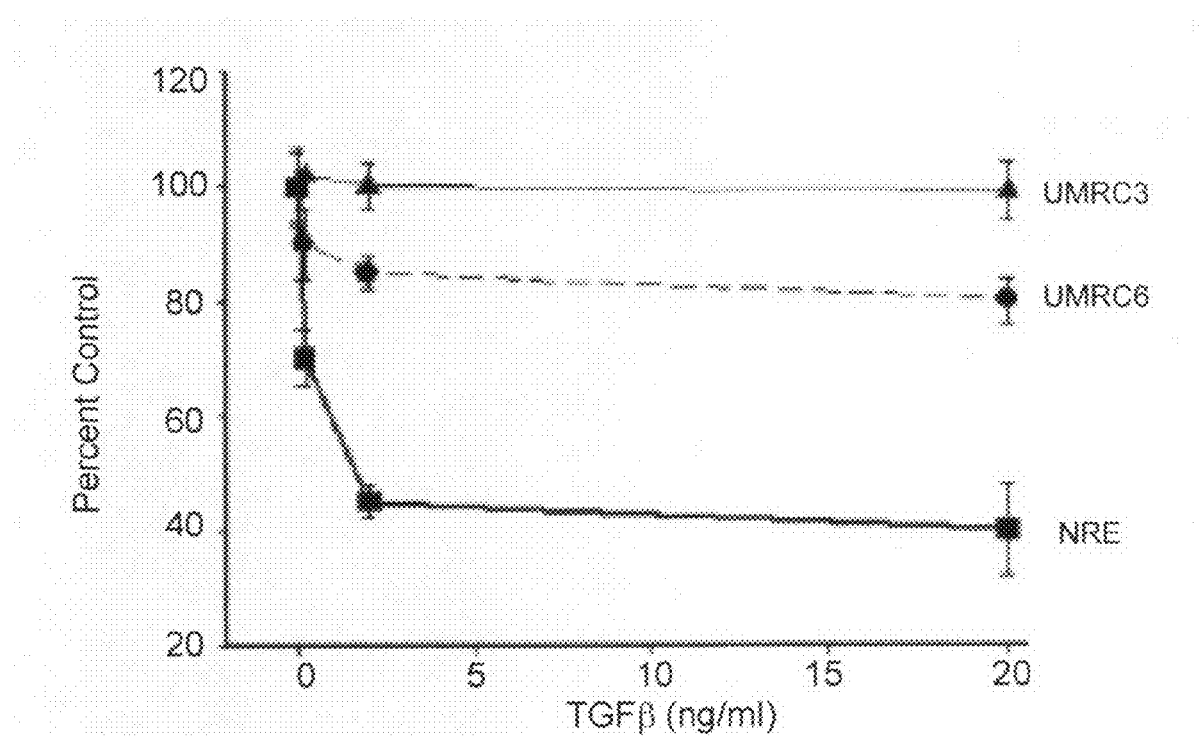
FIGS. 15A-15B show loss of type III TGF-β receptor (TBR3) and type II αreceptor (TBR2) expression in renal tumor cell lines correlate with loss of TGF-β-regulated growth inhibitory and transcriptional responses.

As shown in FIG. 15A (squares), TGF-β1 inhibited the proliferation of normal renal epithelial cells in culture. URMC3 cells expressed neither type II or type III TGF-β receptors and, not surprisingly, were resistant to the inhibitory effects of TGF-β on cell proliferation (triangles, FIG. 15A). UMRC6 cells expressed type II but not type III TGF-β receptors, and were partially resistant to TGF-β1 (circles, FIG. 15A).

Figure 15B:
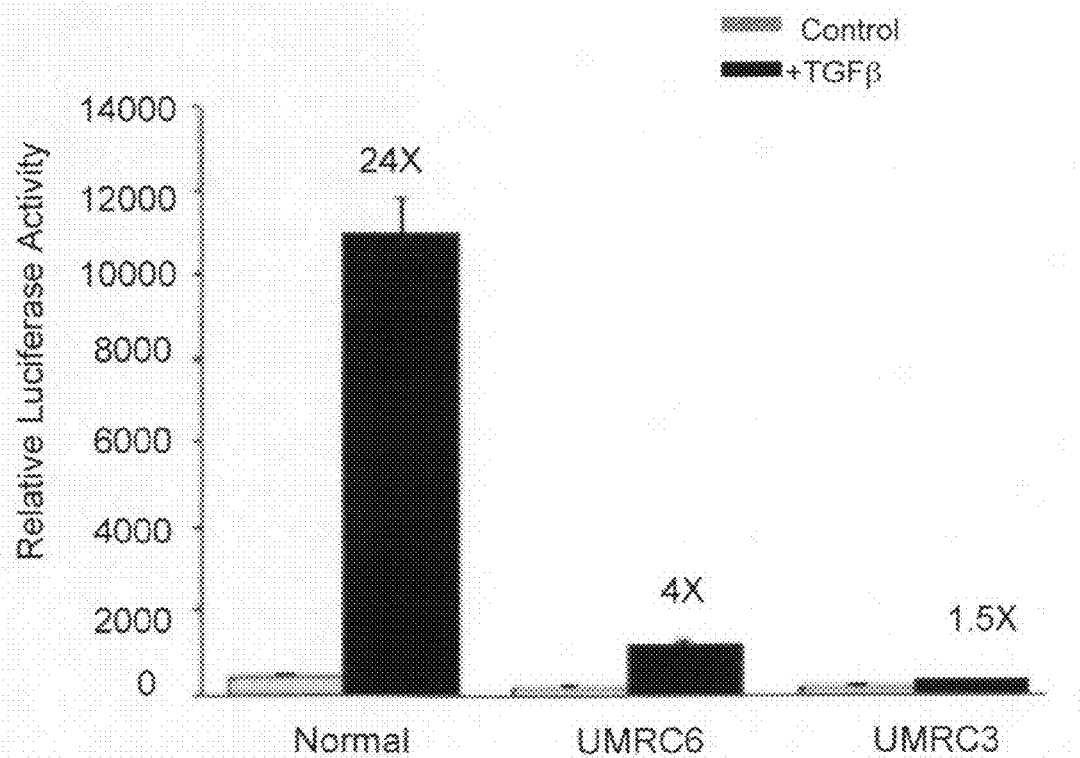

TGF-β transcriptional activity was also measured in the above cell models using transient transfection of the 3TP/lux reporter, which contains an AP-1/Smad3 response element from the PAI-1 promoter. This luciferase reporter construct demonstrates increased transcriptional activity in response to exogenous TGF-β-mediated signal transduction. 3TP/lux was transiently transfected along with SV/renilla luciferase (Promega) into cells using fugene (Roche) as the transfection agent. Cells were treated with or without TGF-β1 24 h after transfection and luciferase activity (Promega Luciferase Assay system and Lumat luminometer) was determined 24 h after TGF-β treatment. Firefly luciferase activity was normalized using the ratio of firefly luciferase/renilla luciferase. As shown in FIG. 15B, normal renal epithelial cells were highly responsive to 2 ng/ml (80 pM) of TGF-β1. UMRC6 cells demonstrated significantly less luciferase activity in response to TGF-β1, and UMRC3 cells were entirely unresponsive.

EXAMPLE 10

Recapitulation of TGF-β Signaling Through Reintroduction of TGF-b Receptor Expression into Renal Cell Carcinoma To test whether reintroduction of TGF-β receptor expression would result in re-establishment of TGF-β signal transduction and reacquisition of TGF-β cellular sensitivity, UMRC3 cells were engineered to express stably either type II TGF-β receptor (+TBR2) alone or type II plus type III TGF-β receptor (+TBR2+TBR3).

Plasmid construction and transfection were described as follows. The complete coding sequences for human type II TGF-β receptor (TBR2) was cloned into the EcoRI/XbaI site of pcDNA3/FLAG. The expression vector was stably transfected into UMRC3 cells using fugene as DNA carrier and genticin as selection antibiotic (Sigma, 1 mg/ml). Ten clones (UMRC3/TBR2) were selected and verified for TBR 2 mRNA and protein expression such as Western analysis using the FLAG antibody (data not shown). From these cell clones, one was to be selected that had equivalent protein expression of TBR2 to that of normal renal epithelial (NRE) and UMRC6 cells.

The type III TGF-β receptor (TBR3) coding sequence was PCR amplified from a plasmid expressing wild-type TBR3 in pSV7d (a gift from Dr C-H Heldin). TBR3 was then cloned into the EcoRI site of pcDNA4/TO/myc-His® (InVitrogen) in the sense and antisense (negative control) orientation. The orientation and sequence of TBR3 was verified. The antisense TBR3 (As TBR3) vector was used as a control. TBR3/pcDNA4/TO/myc-His and As TBR3/pcDNA4/TO/myc-His vectors were stably transfected into UMRC3/TBR2 cells. A clone was selected that demonstrated an equivalent expression of TBR3 mRNA to that of normal renal epithelial cells. As a control for UMRC3+TBR2 and UMRC3+TBR2+ TBR3, wild-type UMRC3 were stably transfected with both pcDNA/FLAG and pcDNA4/TO/myc-His vectors.

Figure 16A:
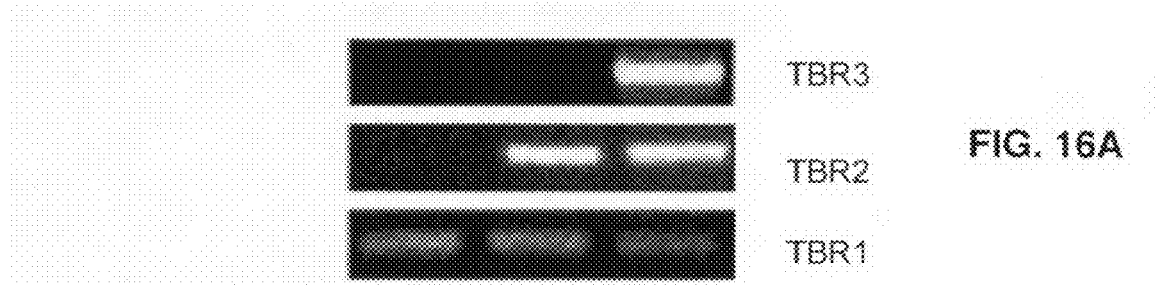
FIG. 16A demonstrates RT-PCR derived mRNA expression of type III αreceptor (TBR3), type II αreceptor (TBR2), and type I αreceptor (TBR1) in UMRC3 cells and cells stably transfected with TBR2 and TBR3.
Figure 16B:
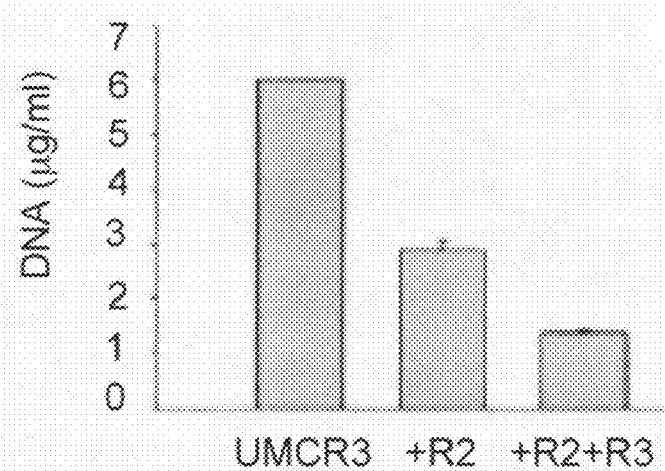
FIG. 16B shows UMRC3 cells stably transfected with type II TGF-β receptor (UMRC3+TBR2) or type II and type III TGF-β receptor (UMRC3+TBR2+TBR3) demonstrated attenuated cell proliferation following the administration of exogenous TGF-β1 as compared to that of UMRC3 cells.

As shown in FIGS. 16A-16B, stable transfection of type II TGF-β receptor (TBR2) alone or type II plus type III TGF-β receptor (TBR2+TBR3) resulted in detectable levels of mRNA for each receptor on RT-PCR analysis. On examining the in vitro growth kinetics of these re-engineered cells, it was noted that reintroduction of TBR2 resulted in a twofold reduction in cell proliferation and reintroduction of both TBR2 and TBR3 resulted in a fourfold reduction in cell proliferation with the addition of exogenous TGF-β.

Figure 16C:
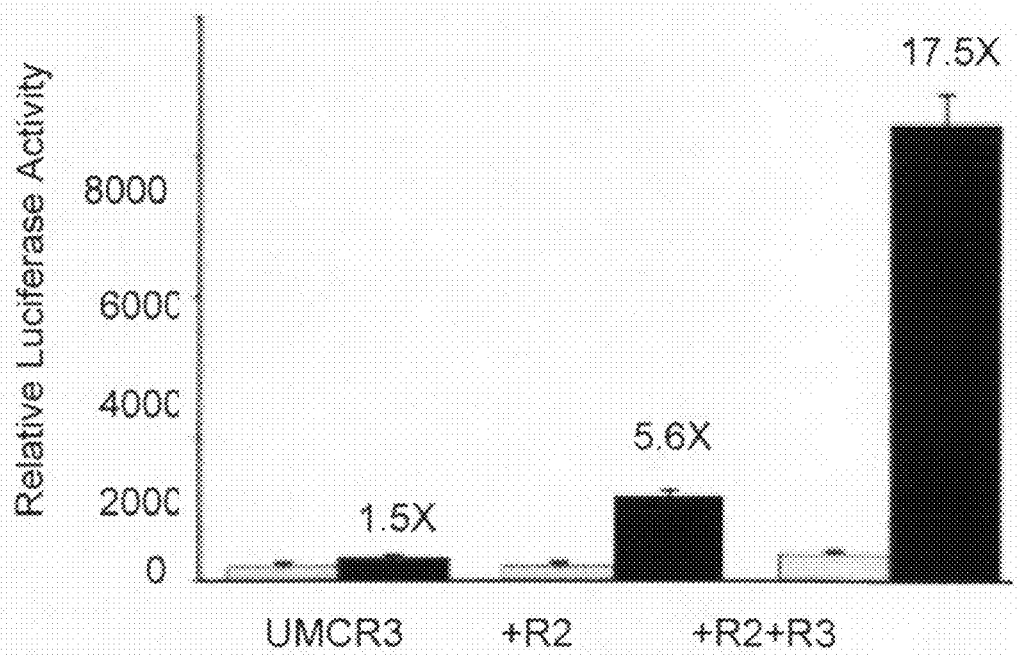
FIG. 16C shows UMRC3 cells, UMRC3+TBR2 cells, and UMRC3+TBR2+TBR3 stable cell lines transfected with 3TP/lux were treated with or without TGF-β and examined for luciferase activity.

The investigators then examined TGF-β-mediated transcriptional activity as a consequence of TGF-β receptor re-expression. As shown in FIG. 16C, reintroduction of TBR2 partially restored transcriptional responsiveness, as evidenced by a 5.6-fold increase in 3TP/lux activity after addition of TGF-β1. Reintroduction of both TBR2 and TBR3 into UMRC3 cells resulted in 17.5-fold increase in 3TP/lux activity after addition of TGF-β1.

Figure 16D:
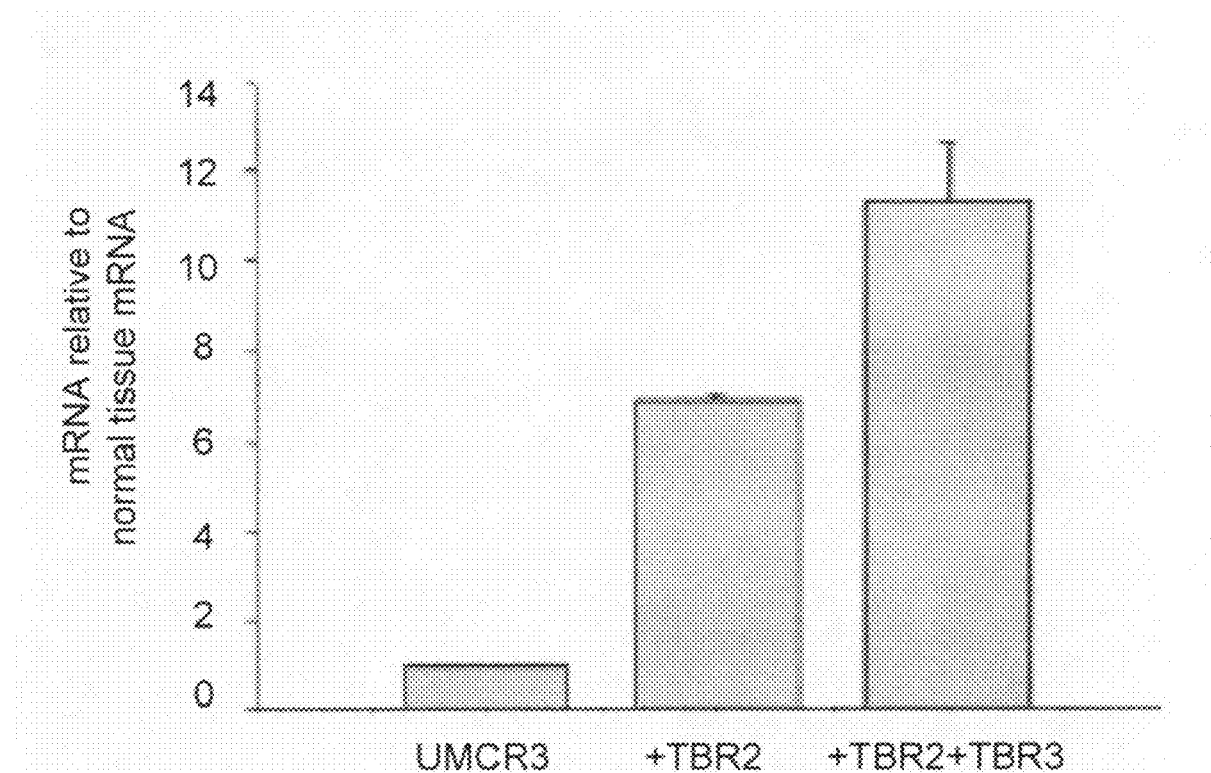
FIG. 16D shows real-time PCR measuring mRNA levels for collagen IV type 6 in UMRC3, UMRC3+TBR2 cells, and UMRC3+TBR2+TBR3 cells in the presence of 2 ng/ml TGF-β1 for 24 h.

To demonstrate reestablishment of TGF-β-regulated gene expression, collagen IV type 6 mRNA expression was examined by real-time PCR in these re-engineered cell lines in the presence of TGF-β1. As shown in FIG. 16D, reexpression of TBR2 in UMRC3 cells results in a sevenfold increase in collagen IV type 6 mRNA levels over that of UMRC3 controls, while reintroduction of both TBR2 and TBR3 enhanced collagen IV type 6 mRNA expression 11-fold. These data are consistent with a number of published reports that indicate expression of TBR3 is essential for full TGF-β responsiveness.

UMRC3 cells have been shown to be tumorigenic in athymic nude mice (Grossman et al., 1985). Anchorage independent growth in soft agar is a well-established in vitro correlate of in vivo tumorigenicity. Colonies formation in soft agar was determined as follows. UMRC3 (pcDNA/FLAG and pcDNA4/T0/myc-His empty vectors), UMRC3+TBR2, or UMRC3+TBR2+TBR3 cells were plated at 1000 cells/60 mm dish in an agarose/FBS/media sandwich in the presence of 2 ng/ml TGF-β. No selection antibodies were added to the agarose media mixture. The cells were incubated for 45 days to insure that no colony formation would occur. Cells were then stained with 0.005% Crystal Violet, photographed, and assessed for number and size of colonies.

Figure 16E:
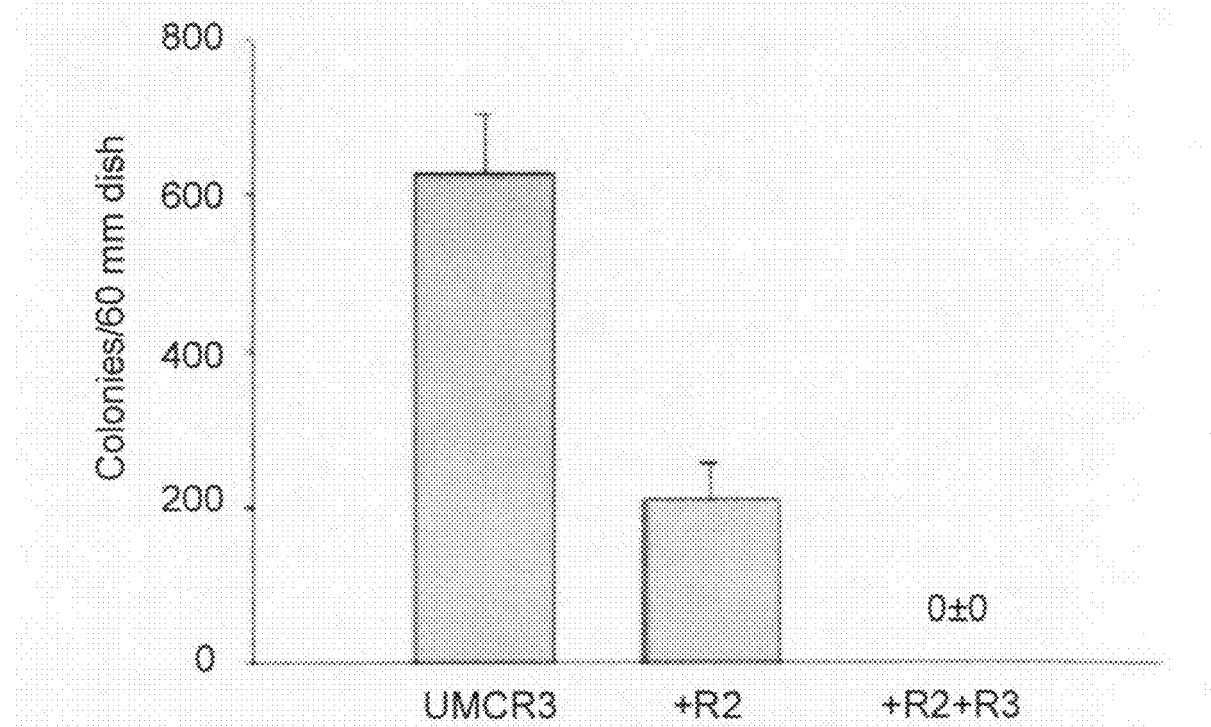
FIG. 16E shows colony formation assay demonstrates that UMRC3+TBR2+TBR3 cells have completely lost anchorage-independent growth, while attenuated growth in UMRC3+TBR2 cells occurs as compared to that of UMRC3 cells. The number of colonies were stained and counted after 45 days of growth. Data are expressed as mean±s.d.

As shown in FIG. 16E, UMRC3 cells demonstrated anchorage independent growth in soft agar. Reintroduction of TBR2 into UMRC3 cells significantly decreased the number and size of colonies that formed in soft agar. Reintroduction of both TBR2 and TBR3 completely abrogated the ability of UMRC3 cells to form colonies in soft agar, even after 45 days in culture. These data demonstrate that reintroduction of TBR2 resensitizes UMRC3 cells to the effects of exogenous TGF-β through reacquisition of TGF-β signal transduction. More interestingly, however, reintroduction of TBR3 in the presence of TBR2 into UMRC3 cells significantly enhanced TGF-β-regulated gene transcription, growth inhibition, and loss of anchorage-independent growth over that seen with reintroduction of TBR2 alone. These data clearly show that renal cell carcinoma cells are TGF-β resistant. Loss of TBR3 expression occurs early and appears to be associated with a relatively less aggressive state that is partially TGF-β responsive. Loss of TBR2 results in frank TGF-β resistance and is associated with acquisition of a more aggressive phenotype.

Figure 17A:
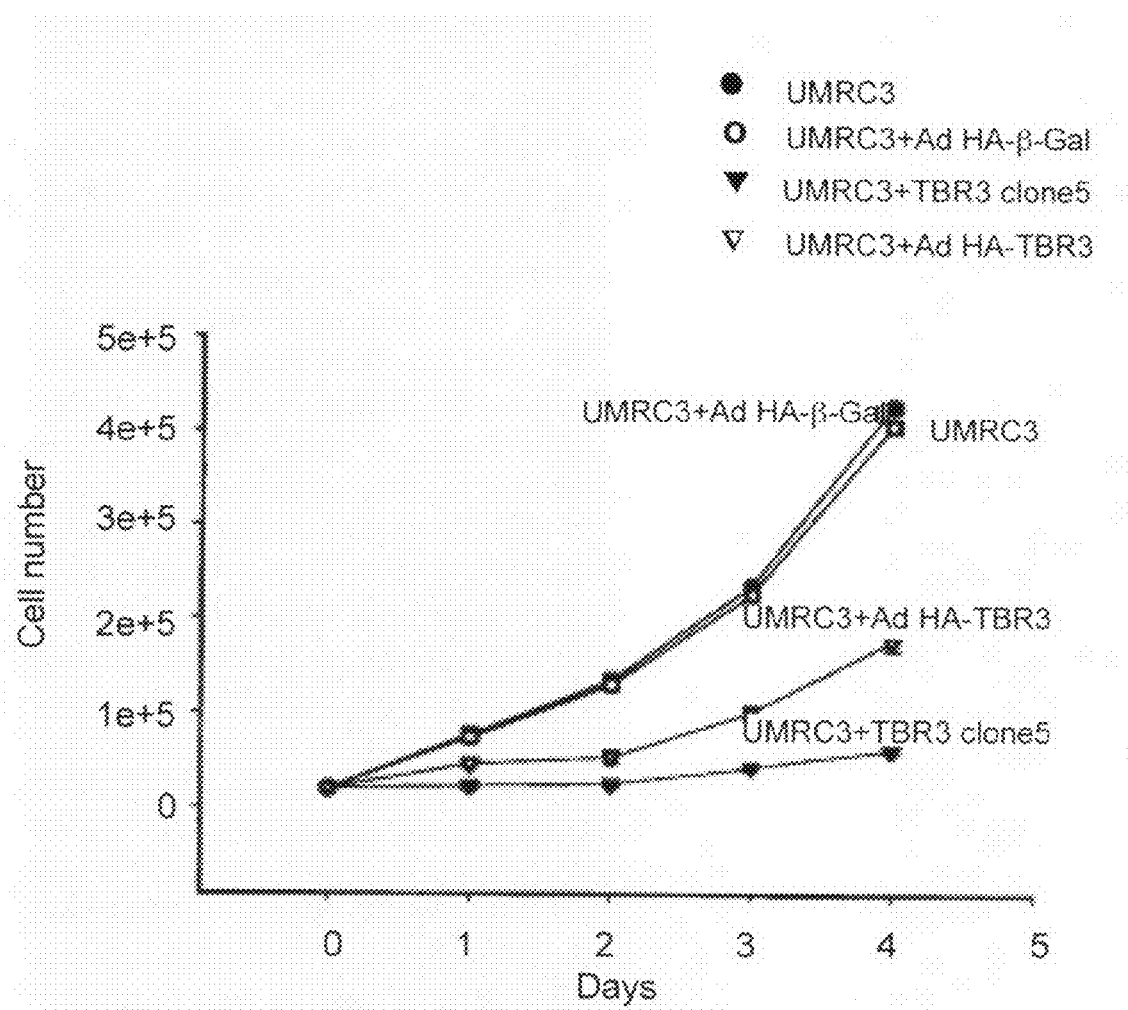
FIG. 17A shows growth inhibition after re-expressing human type III TGF-β receptor (TBR3) in UMRC3 cells. UMRC3 cells were stably transfected with TBR3 or infected using an adenoviral vector expressing TBR3. Cells were plated in culture dishes at 20,000 cells/well. Cell number was determined at the indicated times using a Coulter cell counter.
Figure 17B:
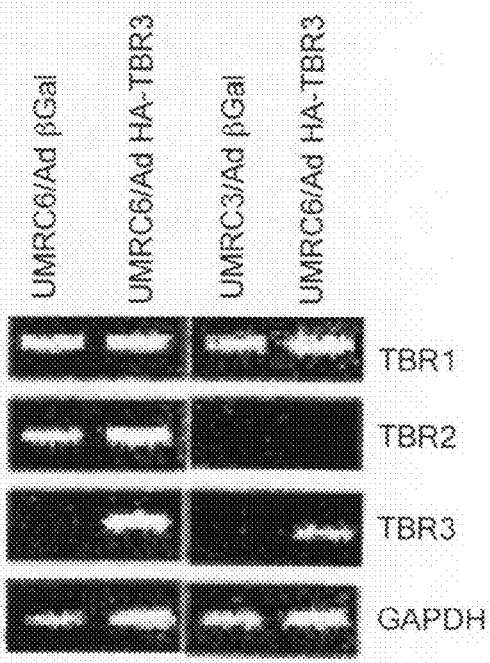
FIG. 17B shows RT-PCR data demonstrating the mRNA expression levels of type I, II, or III TGF-β receptors (TBR1, TBR2, TBR3) in UMRC3 cells in the presence or absence of the adenoviral vector expressing TBR3. Unmodified UMRC3 cells only express TBR1.
Figure 18:
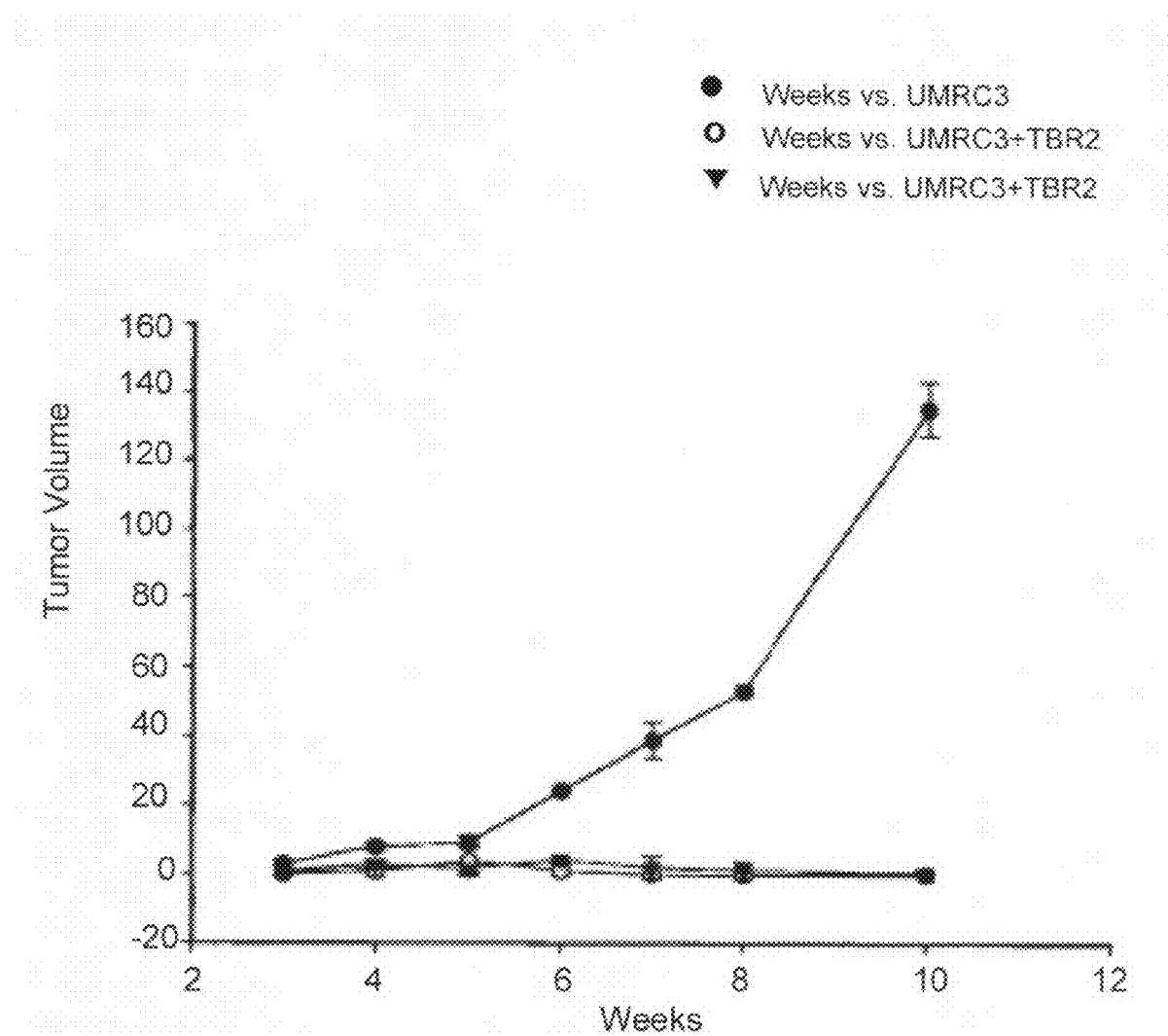
FIG. 18 shows re-expression of human type II or III TGF-β receptors (TBR2 or TBR3) inhibits tumor growth in nude mice. One million UMRC3 cells stably transfected with human type II or type III TGF-β receptors were implanted into nude mice ectopically and tumor growth was measured weekly. Tumor volume (mm³) was calculated by width×length×height×0.5236.

FIGS. 17-18 demonstrate that re-expression of type II or type Ill TGF-β receptor in the highly metastatic human renal cell carcinoma cell line UMRC3 inhibited cell proliferation in cell culture and tumor growth in a nude mouse model. The TGF-β receptors were either re-expressed in a stable vector system or as an adenoviral vector. For clinical purposes, it would be envisioned to treat patients with an adenovirus expressing one or both of the TGF-β receptors to block tumor growth or cause tumor regression.

EXAMPLE 11

Stepwise Sequential Loss of Type III and Type II TGF-β Receptor Expression in Renal Cell Carcinoma With genomic profiling in human renal cell carcinoma, the data presented above demonstrated a stepwise sequential loss of type III and type II TGF-β receptor expression in association with renal cell carcinogenesis and progression. These findings were confirmed by both immunohistochemistry and real-time PCR in patient-matched tissue samples. This clinical observation was brought to the laboratory to identify relevant in vitro models. Using these models, it was demonstrated that loss of type III TGF-β receptor expression resulted in incremental desensitization to TGF-β and attenuation of TGF-β signaling. Subsequent loss of type II TGF-β receptor resulted in complete loss of TGF-β sensitivity. With in vitro modulation of TGF-β receptor expression, it was demonstrated that reconstitution of the TGF-β signaling pathway resulted in significant growth inhibition and loss of the aggressive phenotype.

These experiments are unique in that clinically relevant observations, which are derived from the evaluation of gene expression in normal renal cortical tissue, localized renal cell carcinoma and metastatic renal cell carcinoma, were brought to the laboratory for validation and experimental manipulation in relevant in vitro models. Other investigators have examined human renal cell carcinoma cell lines and identified alterations in the expression of TGF-β signaling pathway intermediaries, but those observations have not been validated in the clinical biology of renal cell carcinoma. To the investigators' knowledge, few studies have methodically examined the expression of all three TGF-βreceptors in patient samples at the protein and mRNA level in an effort to correlate TGF-β receptor expression to disease-specific states of renal cell carcinoma (i.e. localized versus metastatic tumor). A major strength of the present study is that the investigators recognized distinct disease states in renal cell carcinoma, associated them with specific alterations in the TGF-β signaling pathway, and then validated and manipulated the clinical observations in the laboratory.

Although the mechanisms are not well understood, it is clear that TGF-β regulates a large number of diverse biological functions, including cell proliferation, differentiation, cell adhesion, apoptosis, extracellular matrix production, immune regulation, neuroprotection, and early embryonic development. In epithelial cells, the effect of TGF-β is generally to inhibit proliferation, promote cellular differentiation, and regulate interactions with the extracellular matrix. As a direct consequence, aberrations in TGF-β signaling can have a dramatic impact on cellular processes that are critically associated with neoplastic and malignant transformation. Given the well-documented observation that the end result of TGF-β signaling is largely growth inhibitory, it makes intuitive sense that cancer cell would develop mechanisms to escape TGF-β sensitivity. To date, these mechanisms have not been elucidated in human renal cell carcinoma.

Based on the data presented above, the investigators hypothesize that this escape from the growth-inhibitory effects of TGF-β is mediated through the stepwise sequential loss of type III and type II TGF-β receptor expression. To the investigators' knowledge, no one has linked sequential loss of these two types of receptors to carcinogenesis and metastatic progression in oncology. This is the first time that stepwise loss of a single transduction pathway has been associated with important biologic sequelae in a human cancer.

Results presented in the present invention demonstrate that loss of type III TGF-β receptor expression is an early event in renal cell carcinoma biology and that this loss has important sequelae with regard to renal cell carcinoma carcinogenesis and progression. All clinical samples of localized renal cell carcinoma demonstrated loss of type III TGF-β receptor, but had normal expression of type I and type II TGF-β receptors. Replication of this clinical observation in in vitro models demonstrated significant loss of TGF-β sensitivity, manifest as a significant reduction in the growth inhibitory effects of TGF-β1 and significantly reduced TGF-β-mediated transcription. Interestingly, cell lines derived from localized RCC retained type II TGF-β receptor expression and therefore, still demonstrated sensitivity, albeit reduced, to TGF-β. Only with metastatic progression and loss of type II TGF-β receptor expression does the cell become completely resistant to the effects of TGF-β. The investigators hypothesize that this retained, but attenuated, TGF-β signaling seen in local tumors must convey some as yet unrecognized biologic benefit for local tumors that is no longer required, and therefore discarded, with metastatic progression. In fact, this loss of type II TGF-β receptor expression may be an absolute integral component in the cascade of intracellular events that lead to the development of metastatic potential. In keeping with this hypothesis, it has been shown that loss of type I TGF-b receptor expression was one of 40 integral alterations of gene expression to predict for poor prognosis of patients diagnosed with renal cell carcinoma.

In summary, the above results demonstrate a clear link between loss of type III TGF-β receptor expression to a human disease state. Reduced type III TGF-β receptor (TBR3) expression has been reported in human breast tumor cell lines, suggesting that loss of TBR3 expression may be a more ubiquitous phenomena in carcinogenesis, rather than an isolated finding in human RCC biology. The fact that the investigators found down-regulation of TBR3 in every renal cell carcinoma specimen studied to date (35 patients) and that re-expression of TBR3 (in the presence of re-expressed TBR2) completely abolish growth on soft agar suggests an important role for TBR3 in normal renal epithelial homeostasis that must be abrogated for renal cell carcinogenesis and progression to occur. Little attention has been given to TBR3 in normal cell biology or the changes in expression that occur with carcinogenesis and progression. Observations from the present invention would suggest that TBR3 plays an important functional role in signaling and that loss of expression is an important event in the acquisition of the tumorigenic and metastatic phenotype

EXAMPLE 12

Figure 19:
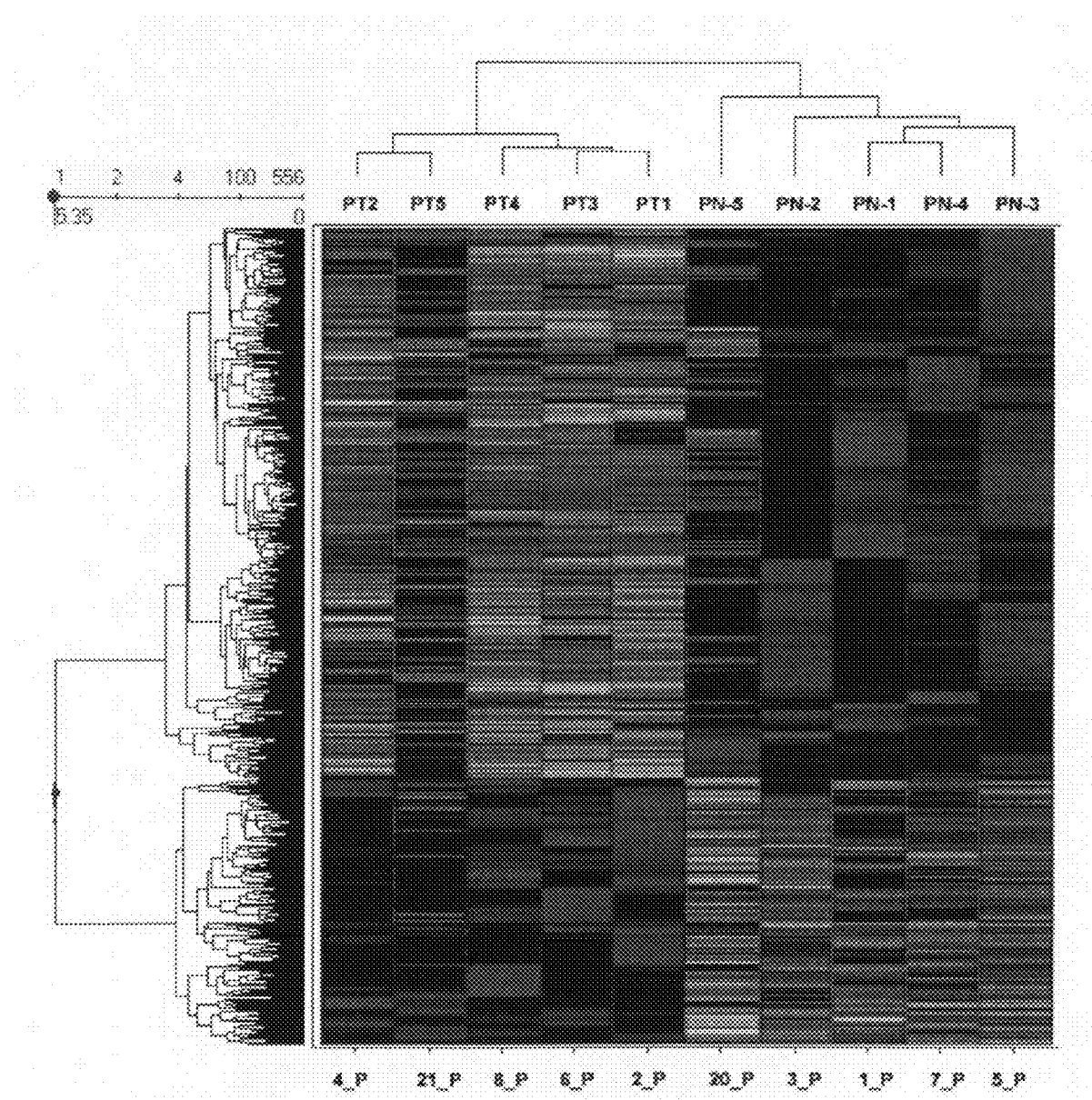
FIG. 19 shows hierarchical clustering of genes expressed in normal renal cortex verse stage I papillary renal cell carcinoma. Red indicates that a gene is highly expressed and green is indicative of low expression.
Figure 20:
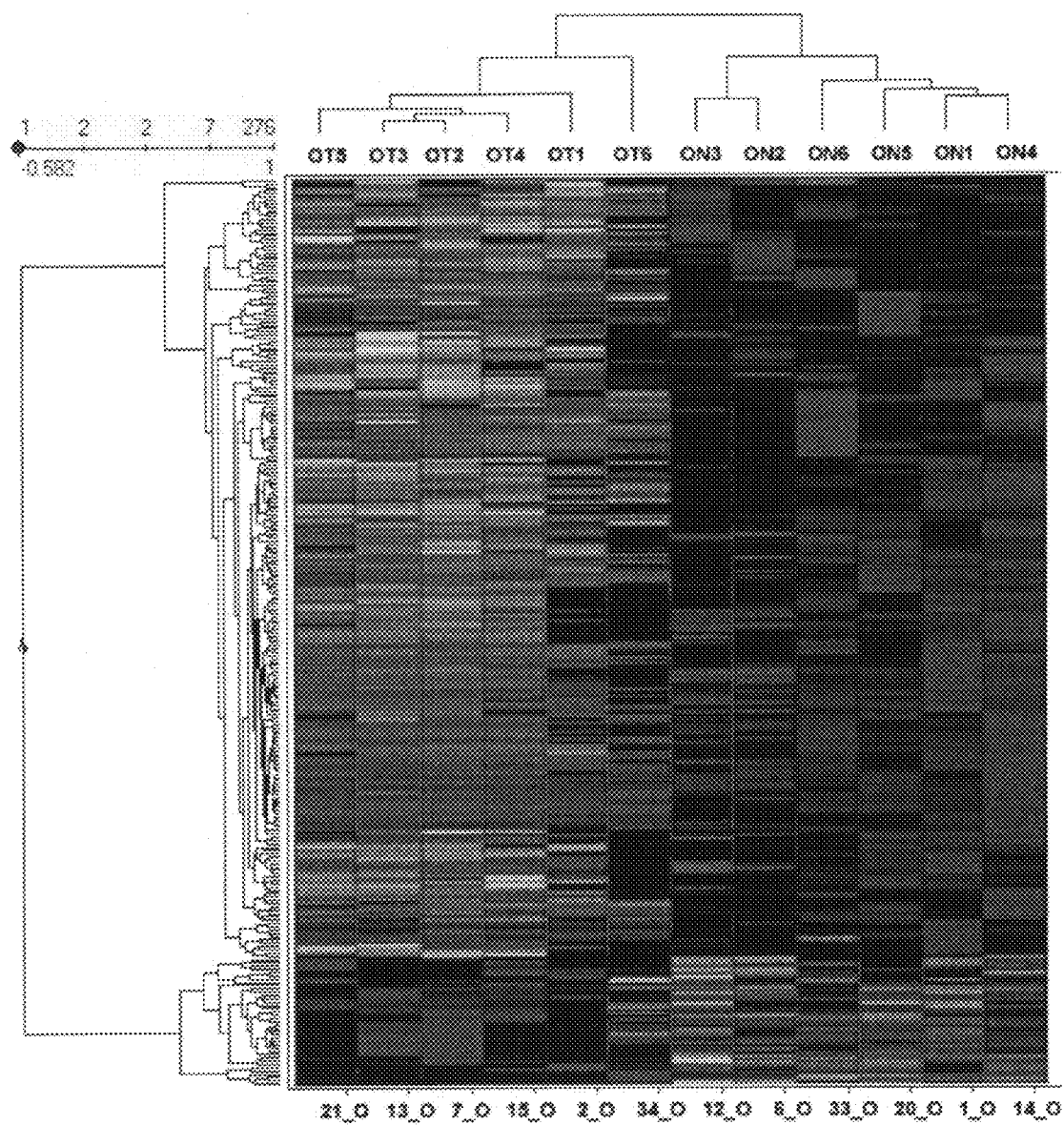
FIG. 20 shows hierarchical clustering of genes expressed in normal renal cortex verse benign oncocytoma. Red indicates that a gene is highly expressed and green is indicative of low expression.
Figure 21:
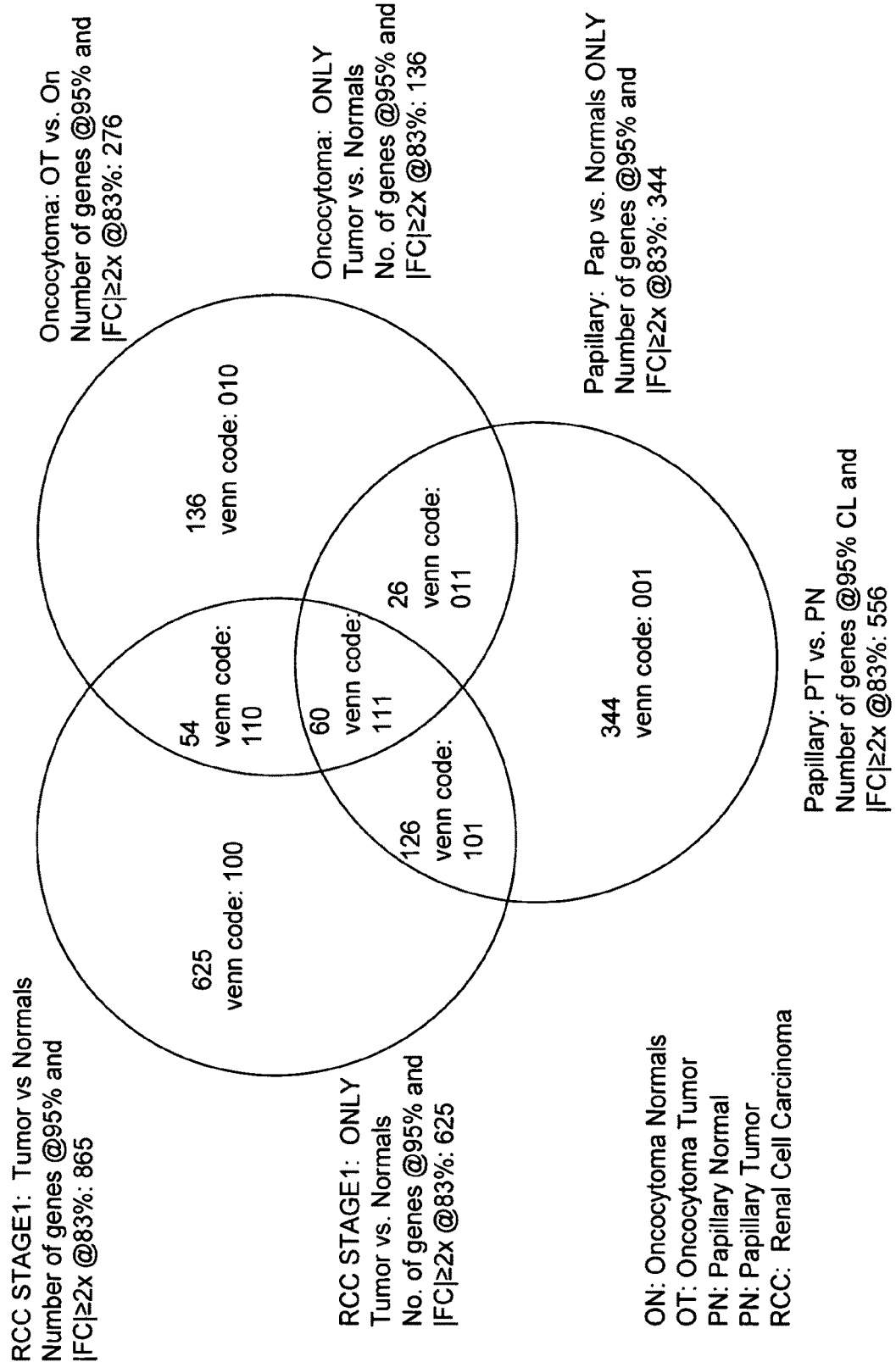
FIG. 21 shows venn analysis of gene distribution among stage I renal cell carcinoma (RCC), oncocytoma and stage I papillary renal cell carcinoma.
Figure 22:
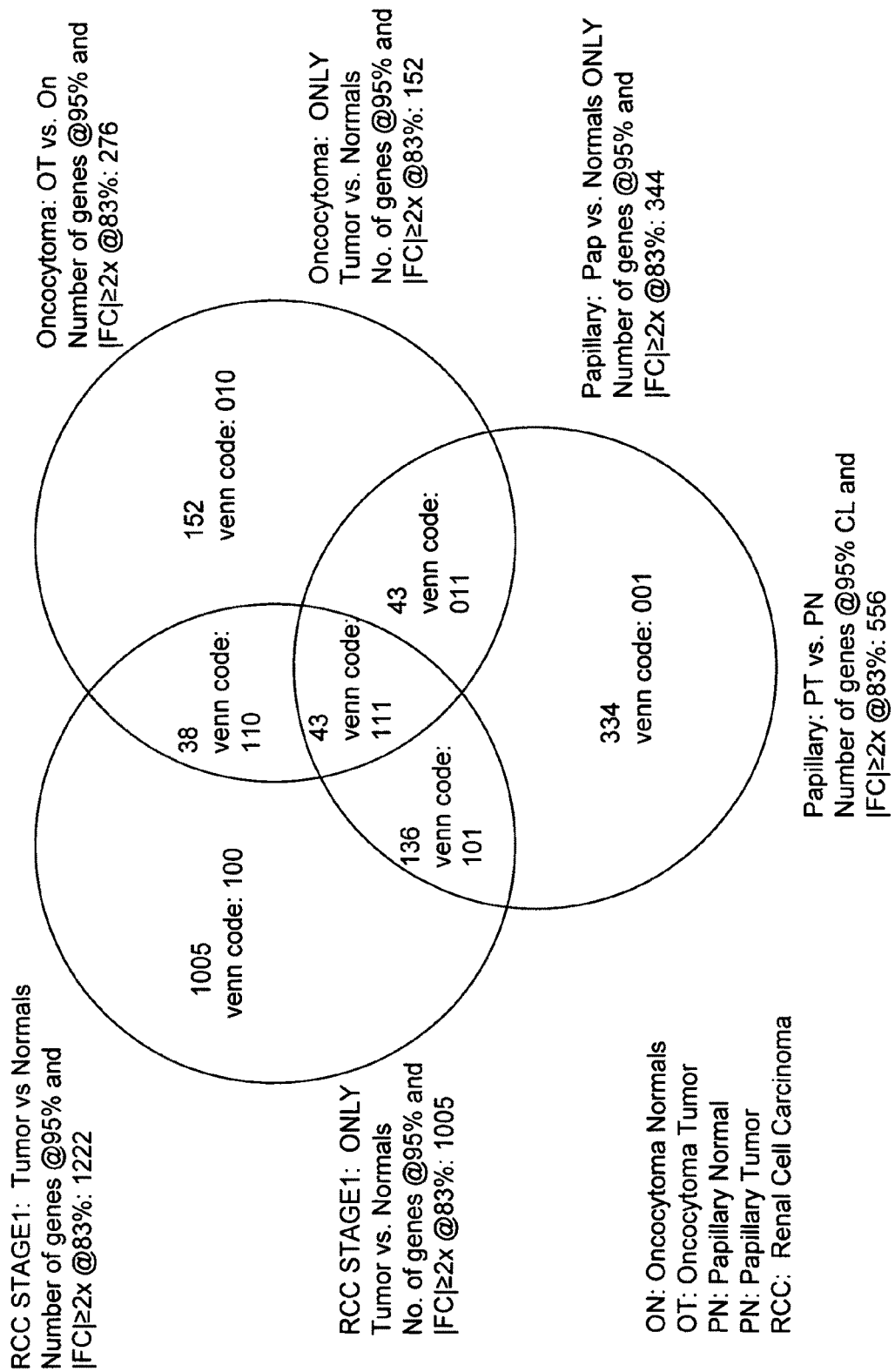
FIG. 22 shows venn analysis of gene distribution among stage II renal cell carcinoma (RCC), oncocytoma and stage I papillary renal cell carcinoma.

Genomic Profiling for Stage I Papillary Renal Cell Carcinoma and Benign Oncocytoma FIG. 19 shows hierarchical clustering of genes over-expressed or down-regulated (with at least 2 fold differences) in stage I papillary renal cell carcinoma verses normal renal cortex. Genes over-expressed and down-regulated in stage I papillary renal cell carcinoma are listed in Table 8 and Table 9 respectively. FIG. 20 shows hierarchical clustering of genes over-expressed or down-regulated (with at least 2 fold differences) in benign oncocytoma verses normal renal cortex. Genes over-expressed and down-regulated in benign oncocytoma are listed in Table 10 and Table 11 respectively. FIG. 21 shows venn analysis of gene distribution among stage I renal cell carcinoma (RCC), oncocytoma and stage I papillary renal cell carcinoma. Genes with at least 2-fold differences in expression were filtered at 95% confidence level (CL) in the following 3 t-tests: stage I RCC vs. normal; oncocytoma vs. normal; and stage I papillary renal cell carcinoma vs. normal. Six hundred twenty five genes were present only in stage I RCC (95% CL), 136 genes were present only in oncocytoma (95% CL), 344 genes were present only in stage I papillary renal cell carcinoma (95% CL), and 60 genes were common to stage I RCC, oncocytoma and stage I papillary renal cell carcinoma. FIG. 22 shows venn analysis of gene distribution among stage II renal cell carcinoma (RCC), oncocytoma and stage I papillary renal cell carcinoma. Genes with at least 2-fold differences in expression were filtered at 95% confidence level (CL) in the following 3 t-tests: stage II RCC vs. normal; oncocytoma vs. normal; and stage I papillary renal cell carcinoma vs. normal. One thousand and five genes were present only in stage II RCC (95% CL), 152 genes were present only in oncocytoma (95% CL), 334 genes were present only in stage I papillary renal cell carcinoma (95% CL), and 43 genes were common to stage II RCC, oncocytoma and stage I papillary renal cell carcinoma.

TABLE 8

Genes With Up-Regulated Expression In stage I Papillary Renal Cell Carcinoma

| Genbank ID | Gene Symbol | Genbank ID | Gene Symbol |
| --- | --- | --- | --- |
| NM_003505 | FZD1 | AC004382 | DKFZP434K046 |
| AL035683 | B4GALT5 | NM_000248 | MITF |
| R56118 | N/A | NM_022154 | SLC39A8 |
| NM_014575 | SCHIP1 | AI436813 | N/A |
| AI694320 | ZNF533 | AF007162 | CRYAB |
| BC031322 | N/A | NM_015392 | NPDC1 |
| BF346665 | N/A | AL136585 | DKFZp761A132 |
| BC004283 | LOC283639 | AB040120 | SLC39A8 |
| AF302786 | GNPTAG | NM_138473 | SP1 |
| AU121975 | PAICS | AU144387 | 182-FIP |
| NM_016315 | GULP1 | NM_022763 | FAD104 |
| AL541302 | SERPINE2 | AI093231 | APBB1IP |
| BG391217 | C9orf80 | NM_000235 | LIPA |
| NM_000700 | ANXA1 | AI817079 | EXOC7 |
| N30188 | N/A | NM_004385 | CSPG2 |
| NM_003651 | CSDA | NM_024801 | TARSH |
| AI830227 | FLII | BF218922 | CSPG2 |
| U20350 | CX3CR1 | BF590263 | CSPG2 |
| NM_005692 | ABCF2 | NM_001233 | CAV2 |
| U34074 | AKAP1 | AB020690 | PNMA2 |
| AB056106 | TARSH | AW188198 | TNFAIP6 |
| AU151483 | CDH6 | NM_007115 | TNFAIP6 |
| BC026260 | TTC3 | AI742838 | DOCK11 |
| AL133001 | SULF2 | AW117264 | N/A |
| NM_003358 | UGCG | AF016266 | TNFRSF10B |
| NM_001282 | AP2B1 | NM_013952 | PAX8 |
| AF322067 | RAB34 | AA771779 | ZFP90 |
| NM_001540 | HSPB1 | W72333 | FLJ21657 |
| N58363 | STATIP1 | H23979 | MOX2 |
| AF072872 | FZD1 | BG542521 | PPM2C |
| BF247552 | SLC38A1 | AF063591 | MOX2 |
| X69397 | CD24 | BF247383 | BMPR2 |
| BC000251 | GSK3B | NM_005114 | HS3ST1 |
| BF691447 | B4GALT5 | BE466145 | N/A |
| AB046817 | SYTL2 | BC005352 | TNFAIP8 |
| AF255647 | DKFZP566N034 | AC002045 | LOC339047 |
| BF344237 | N/A | BC040558 | D2LIC |
| AW242720 | LOC143381 | U13699 | CASP1 |
| AA115485 | MGC3222 | NM_002718 | PPP2R3A |
| NM_006588 | SULT1C2 | BF476502 | MPPE1 |
| NM_000546 | TP53 | BC034275 | LOC253982 |
| N92494 | JWA | AF279145 | ANTXR1 |
| W74580 | MGC3222 | AV724216 | NDRG4 |
| AF131749 | PSK-1 | BG165613 | N/A |
| AW026491 | CCND2 | NM_018205 | LRRC20 |

TABLE 8-continued

Genes With Up-Regulated Expression In stage I Papillary Renal Cell Carcinoma

| Genbank ID | Gene Symbol | Genbank ID | Gene Symbol |
|---|---|---|---|
| NM_012410 | PSK-1 | NM_022083 | C1orf24 |
| NM_002800 | PSMB9 | NM_006169 | NNMT |
| BF512748 | JAK3 | AF141347 | TUBA3 |
| AA404269 | PRICKLE1 | NM_000064 | C3 |
| M33376 | AKR1C1 | AV710838 | BCDO2 |
| AF035321 | DNM1 | AI417917 | EHD2 |
| NM_002862 | PYGB | AI681260 | LILRB1 |
| AF132000 | DKFZP564K1964 | NM_000389 | CDKN1A |
| L07950 | HLA-C | AF288391 | C1orf24 |
| AF114011 | TNFSF13 | NM_002627 | PFKP |
| BF674052 | VMP1 | NM_001975 | ENO2 |
| AI922599 | VIM | NM_030786 | SYNCOILIN |
| AF044773 | BANF1 | NM_006169 | NNMT |
| NM_015925 | LISCH7 | AI417917 | EHD2 |
| NM_001684 | ATP2B4 | NM_006868 | RAB31 |
| AI123348 | CHST11 | L03203 | PMP22 |
| NM_001304 | CPD | AF199015 | VIL2 |
| NM_006762 | LAPTM5 | AI873273 | SLC16A6 |
| NM_000211 | ITGB2 | NM_017821 | RHBDL2 |
| AA995910 | ALOX5 | BF740152 | MYO1F |
| NM_018965 | TREM2 | AA954994 | N/A |
| AL353715 | STMN3 | AI458735 | MGC26717 |
| BC019612 | C20orf75 | NM_003254 | TIMP1 |
| AF086074 | N/A | AI688631 | N/A |
| NM_005045 | RELN | AK026037 | N/A |
| AI935123 | C14orf78 | BG327863 | CD24 |
| AL550875 | C7orf28B | NM_016008 | D2LIC |
| L27624 | TFPI2 | AI394438 | LOC253981 |
| AL574096 | TFPI2 | AA947051 | D2LIC |
| AA005141 | MET | AI819043 | N/A |
| D86983 | D2S448 | AI378044 | UGCG |
| AW439242 | C6orf68 | NM_024576 | OGFRL1 |
| AB000221 | CCL18 | M76477 | GM2A |
| NM_002121 | HLA-DPB1 | NM_002214 | ITGB8 |
| U17496 | PSMB8 | AI879381 | ADCK2 |
| U05598 | AKR1C1 | NM_000152 | GAA |
| BF342851 | D2S448 | H15129 | MEIS4 |
| BF311866 | PTGFRN | L42024 | HLA-C |
| NM_001449 | FHL1 | NM_002178 | IGFBP6 |
| AA954994 | N/A | AI761561 | HK2 |
| Y13710 | CCL18 | AA722799 | DCBLD2 |
| BG170541 | MET | NM_003255 | TIMP2 |
| AB037813 | DKFZp762K222 | NM_000107 | DDB2 |
| D28124 | NBL1 | AV699565 | CTSC |
| NM_021103 | TMSB10 | NM_000861 | HRH1 |
| AI949772 | N/A | | |

TABLE 9

Genes With Down-Regulated Expression In stage I Papillary Renal Cell Carcinoma

| Genbank ID | Gene Symbol | | |
|---|---|---|---|
| AF232217 | N/A | NM_003877 | SOCS2 |
| AI823572 | MGC45438 | AI768894 | CGN |
| AU154994 | SLC13A3 | AW772192 | N/A |
| AW979271 | N/A | AF094518 | ESRRG |
| AF064103 | CDC14A | T40942 | ANGPTL3 |
| AI524125 | PCDH9 | NM_001146 | ANGPT1 |
| AI733474 | GPR155 | AI242023 | N/A |
| AI767756 | HS6ST2 | BF970431 | N/A |
| NM_000412 | HRG | NM_005670 | EPM2A |
| NM_021614 | KCNN2 | AW071744 | KCNJ10 |
| M13149 | HRG | AI928242 | TFCP2L1 |
| H17038 | N/A | AI769774 | LOC155006 |
| NM_002010 | FGF9 | AW274034 | USP9 |
| AI635774 | EMCN | NM_004633 | IL1R2 |
| AW007532 | IGFBP5 | NM_003289 | TPM2 |
| NM_004070 | CLCNKA | BF512388 | C10orf58 |
| NM_014621 | HOXD4 | BC005830 | ANXA9 |
| AI733593 | N/A | NM_000362 | TIMP3 |

TABLE 9-continued

Genes With Down-Regulated Expression In stage I Papillary Renal Cell Carcinoma

| Genbank ID | Gene Symbol | | |
|---|---|---|---|
| NM_020632 | ATP6V0A4 | NM_001438 | ESRRG |
| AI697028 | FLJ90165 | AU146204 | ENPP6 |
| AA897516 | PTGER4 | AA775681 | FLJ23091 |
| NM_024307 | MGC4171 | AI393205 | ACY-3 |
| J02639 | SERPINA5 | AF017987 | SFRP1 |
| NM_000085 | CLCNKB | NM_005951 | MT1H |
| AA058832 | MGC33926 | NM_005950 | MT1G |
| BF059276 | N/A | NM_021805 | SIGIRR |
| BC043647 | LOC284578 | AA557324 | CYP4X1 |
| AL161958 | THY1 | BF528646 | DKFZP564I1171 |
| AL121845 | KIAA1847 | AW340112 | LOC401022 |
| AY079172 | ATP6V0D2 | R73554 | IGFBP5 |
| AA928708 | CYP8B1 | AI826437 | N/A |
| H71135 | ADH6 | AV720650 | KIAA0888 |
| NM_000102 | CYP17A1 | AA780067 | HS3ST3B1 |
| Z92546 | SUSD2 | NM_000640 | IL13RA2 |
| AL558479 | THY1 | AI806338 | TBX3 |
| BC005314 | ALDOB | NM_003155 | STC1 |
| NM_173591 | FLJ90579 | AA931562 | N/A |
| BF510426 | N/A | AI694325 | N/A |
| AF331844 | SOST | AF205940 | EMCN |
| X77737 | SLC4A1 | NM_001290 | LDB2 |
| NM_004392 | DACH1 | NM_016242 | EMCN |
| BC001077 | LOC87769 | AW014927 | CALB1 |
| AA218868 | THY1 | AI758950 | SLC26A7 |
| BF478120 | RECQL5 | AK024256 | KIAA1573 |
| BC041158 | CYP4A11 | BF726212 | ANK2 |
| AI623321 | MTP | AI985987 | SCNN1G |
| AI796189 | PAH | AW242408 | UPP2 |
| NM_021161 | KCNK10 | NM_000860 | HPGD |
| NM_000163 | GHR | BF447963 | KIAA0962 |
| AL136880 | ESPN | BF941499 | GPR116 |
| NM_024426 | WT1 | AW242409 | N/A |
| M61900 | PTGDS | BF509031 | ATP6V1G3 |
| AW963951 | SIAT7C | NM_000934 | SERPINF2 |
| AW340588 | MAN1C1 | BF248364 | AF15Q14 |
| AI263078 | SLC23A3 | AL534095 | FLJ23091 |
| BF130943 | PPAPDC1 | NM_004929 | CALB1 |
| AI732596 | N/A | AI222435 | N/A |
| AA603467 | ZNF503 | NM_005397 | PODXL |
| R41565 | N/A | AI090268 | N/A |
| AI951185 | NR2F1 | AI300520 | STC1 |
| NM_002609 | PDGFRB | BC006236 | MGC11324 |
| NM_006984 | CLDN10 | NM_024609 | NES |
| BG413612 | N/A | NM_002591 | PCK1 |
| D64137 | CDKN1C | NM_005410 | SEPP1 |
| AK026344 | PEPP2 | AB020630 | PPP1R16B |
| AI670852 | PTPRB | AF022375 | VEGF |
| AI693153 | GABRB3 | NM_016246 | DHRS10 |
| NM_001393 | ECM2 | AA873542 | SLC6A19 |
| N93191 | PR1 | U95090 | PRODH2 |
| BC005090 | AGMAT | D26054 | FBP1 |
| NM_000717 | CA4 | AI732994 | MGC13034 |
| D38300 | PTGER3 | NM_000151 | G6PC |
| AI650260 | N/A | AK025651 | PNAS-4 |
| BC024226 | IFRG15 | AF161441 | N/A |
| BC006294 | DHRS10 | AF161454 | APOM |
| NM_003039 | SLC2A5 | NM_022129 | MAWBP |
| AI675836 | SORCS1 | AI733515 | MGC52019 |
| NM_005276 | GPD1 | NM_001443 | FABP1 |
| NM_014298 | QPRT | AI433463 | MME |
| M10943 | MT2A | AL049313 | N/A |
| NM_005952 | MT1X | BF195998 | ALDOB |
| NM_002450 | MT1X | NM_022829 | SLC13A3 |
| NM_002910 | RENBP | NM_000035 | ALDOB |
| BF246115 | MT1F | NM_007287 | MME |
| AF078844 | MT1F | NM_003399 | XPNPEP2 |
| AF170911 | SLC23A1 | NM_000196 | HSD11B2 |
| AF333388 | MT1H | BF431313 | N/A |
| NM_003500 | ACOX2 | NM_004844 | SH3BP5 |
| AA995925 | N/A | NM_003206 | TCF21 |
| NM_001218 | CA12 | AI311917 | DPYS |
| BF432333 | FLJ31196 | AA843963 | PRLR |
| NM_001385 | DPYS | NM_017753 | PRG-3 |
| NM_003052 | SLC34A1 | NM_006633 | IQGAP2 |

TABLE 9-continued

Genes With Down-Regulated Expression In stage I Papillary Renal Cell Carcinoma

| Genbank ID | Gene Symbol | Genbank ID | Gene Symbol |
|---|---|---|---|
| NM_000778 | CYP4A11 | NM_001133 | AFM |
| AL136551 | SESN2 | T90064 | N/A |
| NM_000792 | DIO1 | BF696216 | N/A |
| NM_016725 | FOLR1 | NM_004413 | DPEP1 |
| NM_019101 | APOM | Z98443 | FLJ38736 |
| NM_014270 | SLC7A9 | NM_018456 | EAF2 |
| AF124373 | SLC22A6 | AW771563 | N/A |
| NM_016327 | UPB1 | NM_014495 | ANGPTL3 |
| NM_024734 | CLMN | AI074145 | KMO |
| NM_016527 | HAO2 | NM_000896 | CYP4F3 |
| NM_003645 | SLC27A2 | NM_001072 | UGT1A6 |
| AB051536 | FLJ14957 | AI631993 | N/A |
| NM_025149 | FLJ20920 | NM_000277 | PAH |
| BC005939 | PTGDS | M74220 | PLG |
| AL574184 | HPGD | AI935789 | UMOD |
| NM_000161 | GCH1 | NM_002472 | MYH8 |
| H57166 | N/A | BC020873 | CLCNKA |
| NM_000597 | IGFBP2 | NM_000550 | TYRP1 |
| NM_000790 | DDC | AA806965 | BTNL9 |
| NM_004668 | MGAM | NM_020163 | LOC56920 |
| NM_021027 | UGT1A6 | NM_004490 | GRB14 |
| AF348078 | GPR91 | AA788946 | COL12A1 |
| NM_016347 | NAT8 | AW242315 | N/A |
| AF338650 | PDZK3 | AI735586 | LOC152573 |
| BE221817 | CNTN3 | R88990 | N/A |
| NM_004476 | FOLH1 | NM_003278 | TNA |
| NM_004615 | TM4SF2 | NM_007180 | TREH |
| NM_023940 | RASL11B | AW173045 | TBX2 |
| AI742872 | SLC2A12 | U28049 | TBX2 |
| BC001196 | HS6ST1 | NM_001395 | DUSP9 |
| AW195353 | TFCP2L1 | NM_000336 | SCNN1B |
| NM_003122 | SPINK1 | U43604 | N/A |
| NM_144707 | PROM2 | BC029135 | N/A |
| AI653981 | L1CAM | NM_005414 | SKIL |
| AI796169 | GATA3 | BQ894022 | PDE1A |
| M96789 | GJA4 | NM_013335 | GMPPA |
| N74607 | AQP3 | NM_003221 | TFAP2B |
| NM_014059 | RGC32 | BF057634 | HOXD8 |
| AI572079 | SNAI2 | AA523172 | N/A |
| AI056877 | N/A | AF319520 | ARG99 |
| NM_006206 | PDGFRA | NM_002885 | RAP1GA1 |
| AW771314 | MGC35434 | NM_003361 | UMOD |
| NM_016955 | SLA/LP | NM_000142 | FGFR3 |
| AI569804 | LOC375295 | NM_000893 | KNG1 |
| NM_001584 | C11orf8 | BC029135 | N/A |
| BG261252 | EVI1 | NM_147174 | HS6ST2 |
| NM_006226 | PLCL1 | NM_000218 | KCNQ1 |
| NM_001172 | ARG2 | U03884 | KCNJ1 |
| AL050264 | TU3A | X83858 | PTGER3 |
| BC003070 | GATA3 | BF439270 | N/A |
| AL120332 | MGC20785 | AA911235 | MST1 |
| NM_000459 | TEK | NM_000955 | PTGER1 |
| AW242836 | LOC120224 | NM_022844 | MYH11 |
| AI926697 | Gup1 | BC042069 | N/A |
| NM_000486 | AQP2 | NM_005518 | HMGCS2 |
| AI870306 | IRX1 | NM_001963 | EGF |
| AW264204 | CLDN11 | AI632015 | SLC12A1 |
| BF431989 | THRB | AF339805 | N/A |
| AI459140 | N/A | BF106962 | FAM3B |
| NM_001864 | COX7A1 | NM_005019 | PDE1A |
| AI471866 | SLC7A13 | AU146305 | PDE1A |
| AI653107 | NRK | NM_000663 | ABAT |
| NM_004466 | GPC5 | AU119437 | LOC144997 |
| BF195936 | KRT18L1 | BC036095 | DRP2 |
| NM_022454 | SOX17 | R49295 | N/A |
| AW299531 | HOXD10 | AI623202 | PRDM16 |
| AL137716 | AQP6 | AW452355 | N/A |
| AI332407 | SFRP1 | AA563621 | HSPB6 |
| AL565812 | PTN | X15217 | SKIL |
| AI452457 | LOC199920 | AK095719 | N/A |
| AI281593 | DCN | AI056187 | N/A |
| M21692 | ADH1B | AI668598 | N/A |
| AI660243 | TMPRSS2 | AI700882 | SLC13A3 |
| AI754423 | FLJ38507 | NM_000963 | PTGS2 |
| AA759244 | FXYD4 | AW051712 | N/A |
| U75667 | ARG2 | AL832099 | MGC33190 |
| NM_000930 | PLAT | AK057337 | LOC145820 |
| AF083105 | SOX13 | AW300204 | SLC30A8 |
| NM_013231 | FLRT2 | NM_005856 | RAMP3 |
| BI825302 | PR1 | AI458003 | CYYR1 |
| NM_003012 | SFRP1 | AK026877 | N/A |
| AF138300 | DCN | AI632567 | N/A |
| AU155612 | N/A | U91903 | FRZB |
| BG435302 | EBF | AF352728 | FLJ12541 |
| NM_005978 | S100A2 | BM128432 | IGFBP5 |
| NM_000900 | MGP | NM_003102 | SOD3 |
| AK026748 | DKFZP761M1511 | BE676272 | TACC1 |
| J03208 | DBT | AI692180 | PPFIBP2 |
| NM_002345 | LUM | AL544576 | LOC92162 |
| NM_006623 | PHGDH | NM_017688 | BSPRY |
| AF063606 | my048 | AU146310 | N/A |
| NM_001647 | APOD | AI912976 | RASGRF2 |
| AI935541 | N/A | U83508 | ANGPT1 |
| NM_005558 | LAD1 | L47125 | GPC3 |
| AW138125 | PRODH2 | NM_000663 | ABAT |

TABLE 10

Genes With Up-Regulated Expression In Benign Oncocytoma

| Genbank ID | Gene Symbol | Genbank ID | Gene Symbol |
|---|---|---|---|
| NM_005114 | HS3ST1 | AF178532 | BACE2 |
| AA650558 | GNAS | AI521166 | LOC283104 |
| BF062244 | LIN7A | AA005023 | NOD27 |
| NM_030674 | SLC38A1 | AV725364 | GPRC5B |
| NM_014766 | SCRN1 | AW195581 | GPSM2 |
| BC002471 | CPLX1 | BG503479 | B4GALT6 |
| AF183421 | RAB31 | BF031829 | DSG2 |
| AK022100 | KIAA0256 | AW975728 | SLC16A7 |
| BF508244 | AKR1C2 | NM_022495 | C14orf135 |
| BG772511 | N/A | AA703159 | N/A |
| AB037848 | SYT13 | BF247552 | SLC38A1 |
| AK055769 | N/A | NM_001673 | ASNS |
| T58048 | N/A | NM_024622 | FLJ21901 |
| NM_012105 | BACE2 | AI565054 | N/A |
| AA992805 | LEF1 | AW058459 | LOC134285 |
| AK026420 | DMN | NM_001233 | CAV2 |
| NM_024812 | BAALC | BC036550 | N/A |
| AI057226 | N/A | BE464483 | N/A |
| AW138767 | ELOVL7 | NM_002512 | NME2 |
| NM_013233 | STK39 | AF178532 | BACE2 |

TABLE 11

Genes With Down-Regulated Expression In Benign Oncocytoma

| Genbank ID | Gene Symbol | Genbank ID | Gene Symbol |
|---|---|---|---|
| BF593625 | SYK | AW274034 | USP2 |
| AI310001 | FLJ22789 | NM_147174 | HS6ST2 |
| NM_006206 | PDGFRA | AA074145 | PRODH |
| NM_003740 | KCNK5 | AL049176 | CHRDL1 |
| AW138125 | PRODH2 | NM_020353 | PLSCR4 |
| NM_000336 | SCNN1B | NM_024803 | TUBAL3 |
| BC005314 | ALDOB | D16931 | ALB |
| AI796189 | PAH | NM_019076 | UGT1A10 |
| NM_013363 | PCOLCE2 | AF138303 | DCN |
| NM_004466 | GPC5 | D13705 | CYP4A11 |
| AI627531 | N/A | NM_000587 | C7 |
| U28055 | MSTP9 | R49295 | N/A |
| NM_152759 | MGC35140 | NM_000385 | AQP1 |
| AW052159 | N/A | AI669229 | RARRES1 |
| NM_017712 | PGPEP1 | U36189 | C5orf13 |
| AI961231 | TOX | AL110135 | FLJ14753 |

TABLE 11-continued

Genes With Down-Regulated Expression In Benign Oncocytoma

| Genbank ID | Gene Symbol | Genbank ID | Gene Symbol |
|---|---|---|---|
| AI767962 | BNC2 | AW271605 | N/A |
| AF350881 | TRPM6 | BF358386 | N/A |
| AU146418 | N/A | NM_016270 | KLF2 |
| BE875072 | N/A | AA905508 | LOC128153 |
| AI653981 | L1CAM | NM_021630 | PDLIM2 |
| AI634662 | SLC13A3 | AA915989 | TBC1D13 |
| NM_000486 | AQP2 | AL565812 | PTN |
| AW206292 | AQP2 | AI990790 | N/A |
| AI572079 | SNAI2 | BC041158 | CYP4A11 |
| AI694118 | N/A | NM_138474 | N/A |
| NM_000142 | FGFR3 | NM_002899 | RBP1 |
| U78168 | RAPGEF3 | AK024256 | KIAA1573 |
| AI913600 | UNQ846 | AW779672 | SLC17A1 |
| W93847 | MUC15 | NM_021161 | KCNK10 |
| NM_004616 | TM4SF3 | BF196891 | TPMT |
| AI935789 | UMOD | AY028896 | CARD10 |
| NM_007180 | TREH | NM_018456 | EAF2 |
| AL110152 | CD109 | NM_017806 | FLJ20406 |
| AW051599 | N/A | X59065 | FGF1 |
| AI796169 | GATA3 | AI650353 | DACH1 |
| AF017987 | SFRP1 | AW771563 | N/A |
| BE550027 | DKFZp761N1114 | BF431313 | N/A |
| AA535065 | KIAA1847 | NM_000896 | CYP4F3 |
| NM_003361 | UMOD | BC005090 | AGMAT |
| AI263078 | SLC23A3 | U24267 | ALDH4A1 |
| M13149 | HRG | AI090268 | N/A |
| AF278532 | NTN4 | AW014927 | CALB1 |
| AI632015 | SLC12A1 | AL023553 | PIPPIN |
| NM_000412 | HRG | AL049313 | N/A |
| NM_000893 | KNG1 | AK021539 | NCAG1 |
| BG398937 | KNG | AI220117 | MGST1 |
| AL049977 | CLDN8 | NM_020300 | MGST1 |
| N74607 | AQP3 | NM_022568 | ALDH8A1 |
| AW071744 | KCNJ10 | BE874872 | FAM20C |
| AW015506 | AQP2 | NM_004668 | MGAM |
| AI927000 | SOSTDC1 | BF033242 | CES2 |
| AI471866 | SLC7A13 | BC004542 | PLXNB2 |
| NM_001099 | ACPP | NM_000204 | F |
| NM_005074 | SLC17A1 | NM_004525 | LRP2 |
| AA995925 | N/A | AA442149 | MAF |
| AF352728 | FLJ12541 | NM_000049 | ASPA |
| BF343007 | TFAP2A | AI830469 | TFEC |
| NM_016929 | CLIC5 | NM_003759 | SLC4A4 |
| AA911235 | MST1 | AF169017 | FTCD |
| AA639753 | N/A | AF170911 | SLC23A1 |
| NM_004887 | CXCL14 | AA865601 | LOC123876 |
| AW771565 | AIM1 | AA863031 | MGC32871 |
| AI264671 | N/A | AW136060 | SLC13A2 |
| BF510426 | N/A | NM_003041 | SLC5A2 |
| AV728958 | TLN2 | NM_021924 | MUCDHL |
| T90064 | N/A | AW299568 | N/A |
| AA218868 | THY1 | AI927941 | N/A |
| NM_003104 | SORD | AI433463 | MME |
| AJ292204 | AGXT2 | AL365347 | SLC7A8 |
| AI056359 | MAPT | AA502331 | PRAP1 |
| AL568422 | DZIP1 | NM_024709 | FLJ14146 |
| AF339805 | N/A | AF289024 | FTCD |
| NM_000163 | GHR | NM_017614 | BHMT2 |
| AI042017 | NPL | NM_016347 | NAT8 |
| AW340457 | N/A | NM_000277 | PAH |
| BF431199 | DEHAL1 | NM_000316 | PTHR1 |
| BF432254 | MGC15937 | NM_001091 | ABP1 |
| AI368018 | GPD1 | NM_000790 | DDC |
| AF144103 | CXCL14 | BF217861 | MT1E |
| NM_016725 | FOLR1 | BF447963 | KIAA0962 |
| NM_000050 | ASS | NM_001081 | CUBN |
| AA693817 | N/A | NM_018484 | SLC22A11 |
| NM_004929 | CALB1 | AW192692 | N/A |
| NM_000592 | C4A | BF000045 | TINAG |
| AL574184 | HPGD | BC005830 | ANXA9 |
| AA676742 | DMGDH | NM_025257 | C6orf29 |
| AI631993 | N/A | NM_020973 | GBA3 |
| AI566130 | AK3 | NM_001977 | ENPEP |
| AW024233 | GLYAT | AI632692 | N/A |
| AA873542 | SLC6A19 | BI825302 | PR1 |
| AK026966 | AK3 | L12468 | ENPEP |
| NM_022829 | SLC13A3 | AL571375 | SCD4 |
| NM_005950 | MT1G | AL136858 | ZMYND12 |
| AV700405 | MGC52019 | NM_024027 | COLEC11 |
| AI733515 | MGC52019 | NM_014934 | DZIP1 |
| NM_000860 | HPGD | BG496631 | FBI4 |
| U95090 | PRODH2 | NM_018265 | FLJ10901 |
| NM_001385 | DPYS | AI770035 | UPB1 |
| BG401568 | SLC16A9 | AF177272 | UGT2B28 |
| NM_000846 | GSTA1 | NM_004392 | DACH1 |
| BF195998 | ALDOB | N95363 | CDKN1C |
| NM_004413 | DPEP1 | AF261715 | FOLH1 |
| NM_000151 | G6PC | NM_000042 | APOH |
| NM_006744 | RBP4 | NM_001393 | ECM2 |
| NM_013410 | AK3 | R88990 | N/A |
| NM_000035 | ALDOB | AA557324 | CYP4X1 |
| AK026411 | ALDOB | AF116645 | ALB |
| AL135960 | CYP4A11 | BC015993 | MGC27169 |
| M74220 | PLG | AL558479 | THY1 |
| NM_001713 | BHMT | NM_000785 | CYP27B1 |
| AW614558 | SLC39A5 | AW051926 | AMN |
| Z92546 | SUSD2 | AA928708 | CYP8B1 |
| NM_000778 | CYP4A11 | BE407830 | KIFC3 |
| NM_000792 | DIO1 | AI431643 | RRAS2 |
| AI222435 | N/A | AF001434 | EHD1 |
| D26054 | FBP1 | BC005894 | FMO2 |
| AW025165 | SLC22A8 | NM_006798 | UGT2A1 |
| NM_007287 | MME | BF217861 | MT1E |

The following references were cited herein:

Copland et al., Recent Prog. Horm. Res. 58:25-53 (2003).
Copland et al., Oncogene 22:8053-62 (2003).
Grossman et al., J. Surg. Oncol. 28:237-244 (1985).
Trifillis, Exp. Nephrol. 7:353-359 (1999).

What is claimed is:

1. A method of detecting a renal cell cancer comprising the steps of:
   obtaining one or more biological samples comprising renal tissue or renal cells from an individual;
   determining an RNA gene expression level of secreted frizzled related protein 1; and
   performing statistical analysis on the expression level of said gene as compared to that expressed in normal biological samples comprising renal tissue or renal cells, wherein statistically down-regulated gene expression levels would indicate said individual has papillary or clear cell renal cell cancer.

2. The method of claim 1, wherein statistically down-regulated secreted frizzled related protein 1 gene expression levels would indicate said individual has papillary renal cell cancer.

3. The method of claim 1, wherein statistically down-regulated secreted frizzled related protein 1 gene expression levels would indicate said individual has clear cell renal cell cancer.

* * * * *